United States Patent
Karger et al.

[11] Patent Number: 5,872,010
[45] Date of Patent: Feb. 16, 1999

[54] MICROSCALE FLUID HANDLING SYSTEM

[75] Inventors: Barry L. Karger, Newton; Frantisek Foret, Malden; Paul M. Zavracky, Norwood; E. Nicol McGruer, Dover; Qifeng Xue, Somerville; Yuriy M. Dunayevskiy, Malden, all of Mass.

[73] Assignee: Northeastern University, Boston, Mass.

[21] Appl. No.: 675,177

[22] Filed: Jul. 3, 1996

[51] Int. Cl.⁶ .......................... G01N 24/00; G01N 30/00
[52] U.S. Cl. .............................. 436/173; 422/58; 422/59; 422/68.1; 422/69; 422/70; 422/10; 436/52; 436/86; 436/87; 436/89; 436/91; 436/93; 436/94; 436/161; 436/172; 436/174; 436/175; 436/177; 436/183; 210/198.2
[58] Field of Search .............................. 422/100, 58, 59, 422/68.1, 69, 70, 81, 82.01, 82.05, 82.08, 82.09; 436/52, 86, 87, 89, 91, 93, 94, 161, 172, 173, 174, 175, 177, 183; 210/198.2

[56] References Cited

U.S. PATENT DOCUMENTS

| | | | |
|---|---|---|---|
| 3,538,744 | 11/1970 | Karasek | 73/23.1 |
| 3,738,759 | 6/1973 | Dittrich et al. | 356/246 X |
| 3,915,652 | 10/1975 | Natelson | 422/65 |
| 4,056,324 | 11/1977 | Göhde | 356/246 |
| 4,356,722 | 11/1982 | Bunce et al. | 73/53 |

(List continued on next page.)

FOREIGN PATENT DOCUMENTS

| | | |
|---|---|---|
| 0637998 | 7/1996 | European Pat. Off. . |
| 0639223 | 7/1996 | European Pat. Off. . |
| 4318407 | 12/1994 | Germany . |
| 2260282 | 4/1993 | United Kingdom . |
| 9203726 | 3/1992 | WIPO . |
| WO 9604547 | 2/1996 | WIPO . |
| WO 9614933 | 5/1996 | WIPO . |
| WO 9614934 | 5/1996 | WIPO . |
| WO 9615269 | 5/1996 | WIPO . |

OTHER PUBLICATIONS

Y. Yoshida et al. *HRC CC, J. High Resolut. Chromatogr. Chromatogr. Commun.* 1980, 3, 16–20.
A. Manz et al. *Sens. Actuators B 1990*, B1, 249–255.
W. Nichols et al. *LC–GC 1992*, 10, 676, 678, 680, 682, 684–686.
S. Cowen et al. in "Micro Total Analysis Systems, Proceedings TAS '94 Workshop" A. Van den Berg et al. Ed, Kluwer; Dordrecht, Netherlands, pp. 295–298.
G. Ocvirk et al. *Anal. Methods Instrum.* 1995, 2, 74–82.
K. Petersen *Tech. Dig.–Int. Electron Devices Meet.* 1996, 239–242.
J.B. Angell et al. *Scientific American 1983*, Apr., pp. 44–55.
A. Figueroa et al. *J. Chromatogr.* 1986, 371, 335–352.
E.B. Overton et al. EPA Report. 1988 EPA/600/D–89/189, 395–398.
A. Manz et al. *Trends Angl. Chem.* 1991, 10, 144–149.
S. Sjölander et al. *Anal. Chem.* 1991, 63, 2338–2345.

(List continued on next page.)

*Primary Examiner*—Arlen Soderquist
*Attorney, Agent, or Firm*—Weingarten, Schurgin, Gagnebin & Hayes LLP

[57] ABSTRACT

A microscale fluid handling system that permits the efficient transfer of nanoliter to picoliter quantities of a fluid sample from the spatially concentrated environment of a microfabricated chip to "off-chip" analytical or collection devices for further off-chip sample manipulation and analysis is disclosed. The fluid handling system is fabricated in the form of one or more channels, in any suitable format, provided in a microchip body or substrate of silica, polymer or other suitable non-conductive material, or of stainless steel, noble metal, silicon or other suitable conductive or semiconductive material. The microchip fluid handling system includes one or more exit ports integral with the end of one or more of the channels for consecutive or simultaneous off-chip analysis or collection of the sample. The exit port or ports may be configured, for example, as an electrospray interface for transfer of a fluid sample to a mass spectrometer.

37 Claims, 15 Drawing Sheets

U.S. PATENT DOCUMENTS

| | | | |
|---|---|---|---|
| 4,366,118 | 12/1982 | Bunce et al. | 422/57 |
| 4,369,664 | 1/1983 | Bunce et al. | 73/864.12 |
| 4,459,267 | 7/1984 | Bunce et al. | 422/100 |
| 4,593,728 | 6/1986 | Whitehead et al. | 141/98 |
| 4,708,782 | 11/1987 | Andresen et al. | 204/299 R |
| 4,879,097 | 11/1989 | Whitehead et al. | 422/67 |
| 4,891,120 | 1/1990 | Sethi et al. | 204/299 R |
| 4,908,112 | 3/1990 | Pace | 204/299 R |
| 4,983,038 | 1/1991 | Ohki et al. | 356/246 |
| 5,110,745 | 5/1992 | Kricka et al. | 436/87 |
| 5,126,022 | 6/1992 | Soane et al. | 204/180.1 |
| 5,132,012 | 7/1992 | Miura et al. | 210/198.2 |
| 5,180,480 | 1/1993 | Manz | 204/299 R |
| 5,245,185 | 9/1993 | Busch et al. | 250/288 |
| 5,269,900 | 12/1993 | Jorgenson et al. | 204/299 R |
| 5,283,036 | 2/1994 | Hofmann et al. | 422/70 |
| 5,296,114 | 3/1994 | Manz | 204/180.1 |
| 5,296,375 | 3/1994 | Kricka et al. | 435/291 |
| 5,302,533 | 4/1994 | Kricka | 436/537 |
| 5,304,487 | 4/1994 | Wilding et al. | 435/291 |
| 5,306,621 | 4/1994 | Kricka | 435/7.91 |
| 5,328,578 | 7/1994 | Gordon | 204/180.1 |
| 5,332,481 | 7/1994 | Guttman | 204/182.8 |
| 5,338,427 | 8/1994 | Shartle et al. | 204/299 R |
| 5,349,186 | 9/1994 | Ikonomou et al. | 250/288 |
| 5,374,834 | 12/1994 | Geis et al. | 257/239 |
| 5,376,252 | 12/1994 | Ekström et al. | 204/299 R |
| 5,387,329 | 2/1995 | Foos et al. | 204/415 |
| 5,401,376 | 3/1995 | Foos et al. | 204/415 |
| 5,401,963 | 3/1995 | Sittler | 250/288 |
| 5,415,841 | 5/1995 | Dovichi et al. | 422/68.1 |
| 5,421,980 | 6/1995 | Guttman | 204/299 R |
| 5,427,946 | 6/1995 | Kricka et al. | 435/291 |
| 5,429,734 | 7/1995 | Gajar et al. | 204/299 R |
| 5,486,335 | 1/1996 | Wilding et al. | 422/55 |
| 5,498,392 | 3/1996 | Wilding et al. | 422/68.1 |
| 5,500,071 | 3/1996 | Kaltenbach et al. | 210/198.2 |
| 5,512,131 | 4/1996 | Kumar et al. | 156/655.1 |
| 5,512,451 | 4/1996 | Kricka | 435/28 |

OTHER PUBLICATIONS

B.H. Van der Schoot et al. *Anal. Methods Instrum.* 1993, 1, 38–42.

D.J. Harrison et al. *Sens. Actuators, B* 1993, 10, 107–116.

R.D. Smith et al. *J. Toxicol. Environ. Health* 1993, 40, 147–158.

A. Manz et al. *J. High Resolut. Chromatogr.* 1993, 16, 433–436.

M. Elwenspoek et al. *Analysis* 1994, 22, M9–M12.

S.J. Doherty et al. *LC–GC* 1994, 12, 846–850.

S.C. Jacobson et al. *Anal. Chem.* 1994, 66, 1114–1118.

Y.–H. Chu et al. *J. Am. Chem. Soc.* 1996, 118, 7827–7835.

Q. Xue et al. *Anl. Chem.* 1997, 69, 426–430.

Andren et al., "Micro–Electrospray: Zeptomole/Attomole per Microliter Sensitivity of Peptides," *J. Am. Soc. Mass. Spectrom.* 5:867–869 (1994).

Burggraf et al., "Synchronized Cyclic Capillary Electrophoresis—A Novel Approach to Ion Separations in Solution," *Journal of High Resolution Chromatography* 16:594–596 (1993).

Cheng et al., "Chip PCR. II. Investigation of different PCR amplification systems in microfabricated silicon–glass chips," *Nucleic Acids Research* 24:380–385 (1996).

Davis et al., "A Microscale Electrospray Interface for On–Line, Capillary Liquid Chromatography/Tandem Mass Spectrometry of Complex Peptide Mixtures," *Anal. Chem.* 67:4549–4556 (1995).

Deml et al., "Electric Sample Splitter for Capillary Zone Electrophoresis," *Journal of Chromatography* 320:159–165 (1985).

Effenhauser et al., "High–Speed Separation of Antisense Oligonucleotides on a Micromachined Capillary Electrophoresis Device," *Anal. Chem.* 66:2949–2953 (1994).

Effenhauser et al., "Glass Chips for High–Speed Capillary Electrophoresis Separations with Submicrometer Plate Heights," *Anal. Chem.* 65:2637–2642 (1993).

Effenhauser et al., "Manipulation of Sample Fractions on a Capillary Electrophoresis Chip," *Anal. Chem.* 67:2284–2287 (1995).

Emmett et al., "Micro–Electrospray Mass Spectrometry: Ultra–High–Sensitivity Analysis of Peptides and Proteins," *J. Am. Soc. Mass. Spectrom.* 5:605–613 (1994).

Fan et al., "Micromachining of Capillary Electrophoresis Injectors and Separators on Glass Chips and Evaluation of Flow at Capillary Intersections," *Anal. Chem.* 66:177–184 (1994).

Fang et al., "On–Line Time–of–Flight Mass Spectrometric Analysis of Peptides Separated by Capillary Electrophoresis," *Anal. Chem.* 66:3696–3701 (1994).

Gale et al., "Small Volume and Low Flow–rate Electrospray Ionization Mass Spectrometry of Aqueous Samples," *Rapid Communications in Mass Spectrometry* 7:1017–1021 (1993).

Harrison et al., "Capillary Electrophoresis and Sample Injection Systems Integrated on a Planar Glass Chip," *Anal. Chem.* 64:1926–1932 (1992).

Harrison et al., "Micromachining a Minaiaturized Capillary Electrophoresis–Based Chemical Analysis System on a Chip," *Science* 261:895–897 (1993).

Harrison et al., "Rapid Separation Of Fluorescein Derivative Using A Micromachined Capillary Electrophoresis System," *Anal. Chim. Acta* 283:361–366 (1993).

Jacobson et al., "Microchip electrophoresis with sample stacking," *Electrophoresis* 16:481–486 (1995).

Jacobson et al., "Microchip Capillary Electrophoresis with an Integrated Postcolumn Reactor," *Anal. Chem.* 66:3472–3476 (1994).

Jacobson et al., "Fused Quartz Substrates for Microchip Electrophoresis," *Anal. Chem.* 67:2059–2063 (1995).

Jacobson et al., "Integrated Microdevice for DNA Restriction Fragment Analysis," *Anal. Chem.* 68:720–723 (1996).

Jacobson et al., "Effects of Injection Schemes and Column Geometry on the Performance of Microchip Electrophoresis Devices," *Anal. Chem.* 66:1107–1113 (1994).

Jacobson et al., "High–Speed Separations on a Microchip," *anal. Chem.* 66:1114–1118 (1994).

Jacobson et al., "Open Channel Electrochromatrography on a Microchip," *Anal. Chem.* 66:2369–2373 (1994).

Jansson et al., "Micro Vials on a Silicon Wafer for Sample Introduction in Capillary Electrophoresis," *J. Chromatograph.* 626:310–314 (1992).

Ko et al., In Sensors: A Comprehensive Survey; Granke, T., Ko, W.H., Eds; *VCH Press:* Weinheim, Germany 1:107–168 (1989).

Körner et al., "Nano Electrospray Combined with a Quadrupole Ion Trap for the Analysis of Peptides and Protein Digests," *J. Am. Soc. Mass. Spectrom.* 7:150–156 (1996).

Koutny et al., "Microchip Electrophoretic Immunoassay for Serum Cortisol," *Anal. Chem.* 68:18–22 (1996).

Kriger et al., "Durable Gold–Coated Fused Silica Capillaries for Use in Electrospray Mass Spectrometry," *Anal. Chem.* 67:385–389 (1995).

Manz et al., "Planar Chip Technology for Capillary Electrophoresis," *J. Anal. Chem.* 348:567–571 (1994).

Manz et al., "Planar Chips Technology for Miniaturization and Integration of Separation Techniques into Monitoring Systems," *J. Chromatograph.* 593:253–258 (1992).

Olivares et al., "On–Line Mass Spectrometric Detection for Capillary Zone Electrophoresis," *Anal. Chem.* 59:1230–1232 (1987).

Raymond et al., "Continuous Sample Pretreatment Using a Free–Flow Electrophoresis Device Integrated onto a Silicon Chip," *Anal. Chem.* 66:2858–2865 (1994).

Roeraade, "Nano–Sized System for Bioanalysis," *The Eighth International Sysmposium On HPCE,* Orlando, Florida, USA.

Seiler et al., "Electroosmotic Pumping and Valveless Control of Fluid Flow within a Manifold of Capillaries on a Glass Chip," *Anal. Chem.* 66:3485–3491 (1994).

Seiler et al., "Planar Glass Chips for Capillary Electrophoresis: Repetitive Sample Injection, Quantitiation, and Separation Efficiency," *Anal. Chem.* 65:1481–1488 (1993).

Shoffner et al., "Chip PCR. I. Surface Passivation of Microfabricated Silicon–Glass Chips for PCR," *Nucleic Acids Research* 24:375–379 (1996).

Smith et al., "Improved Electrospray Ionization Interface for Capillary Zone Elctrophoresis—Mass Spectrometry," *Anal. Chem.* 60:1948–1952 (1988).

Wahl et al., "Sheathless Capillary Elctrophoresis–Electrospray Ionization Mass Spectrometry Using 10 $\mu$m I.D. Capillaries: Analyses of Trypitic Digests of Cytochrome C," *J. Chromatograph.* 659:217–222 (1994).

Valaskovic et al., "Attomole–Sensitivity Electrospray Source for Large–Molecule Mass Spectrometry," *Anal. Chem.* 67:3802–3805 (1995).

Wilm et al., "Electrospray and Taylor–Cone Theory, Dole's Beam of Macromolecules at Last?," *International Journal of Mass Spectrometry and Ion Processes* 136:167–180 (1994).

Woolley et al., "Ultra–High–Speed DNA Fragment Separations Using Microfabricated Capillary Array Electrophoresis Chips," *Proc. Natl. Acad. Aci. USA* 91:11248–11352 (1994).

Woolley et al., "Ultra–High–Speed DNA Sequencing Using Capillary Electrophoresis Chips," *Anal. Chem.* 67:3676–3680 (1995).

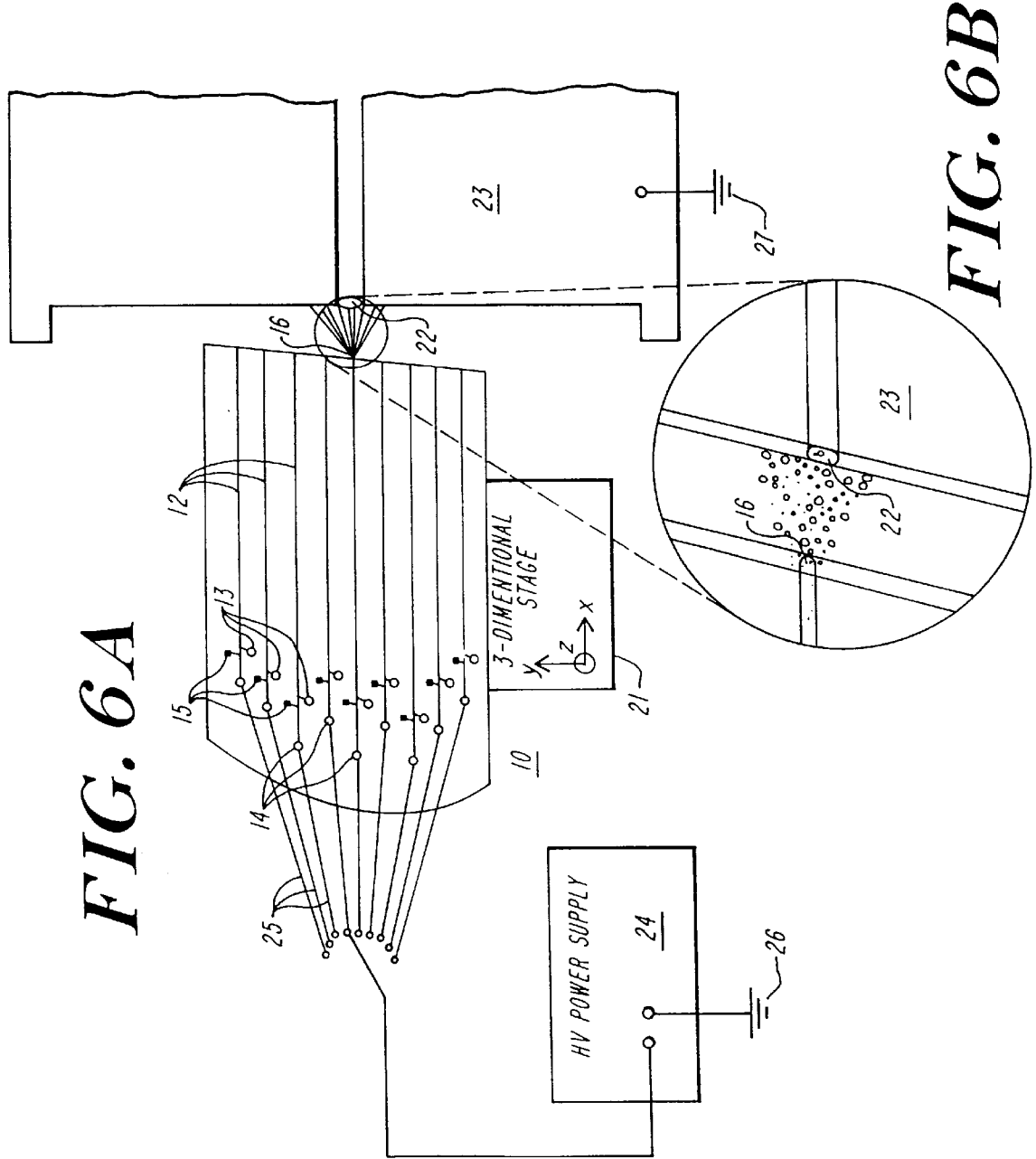

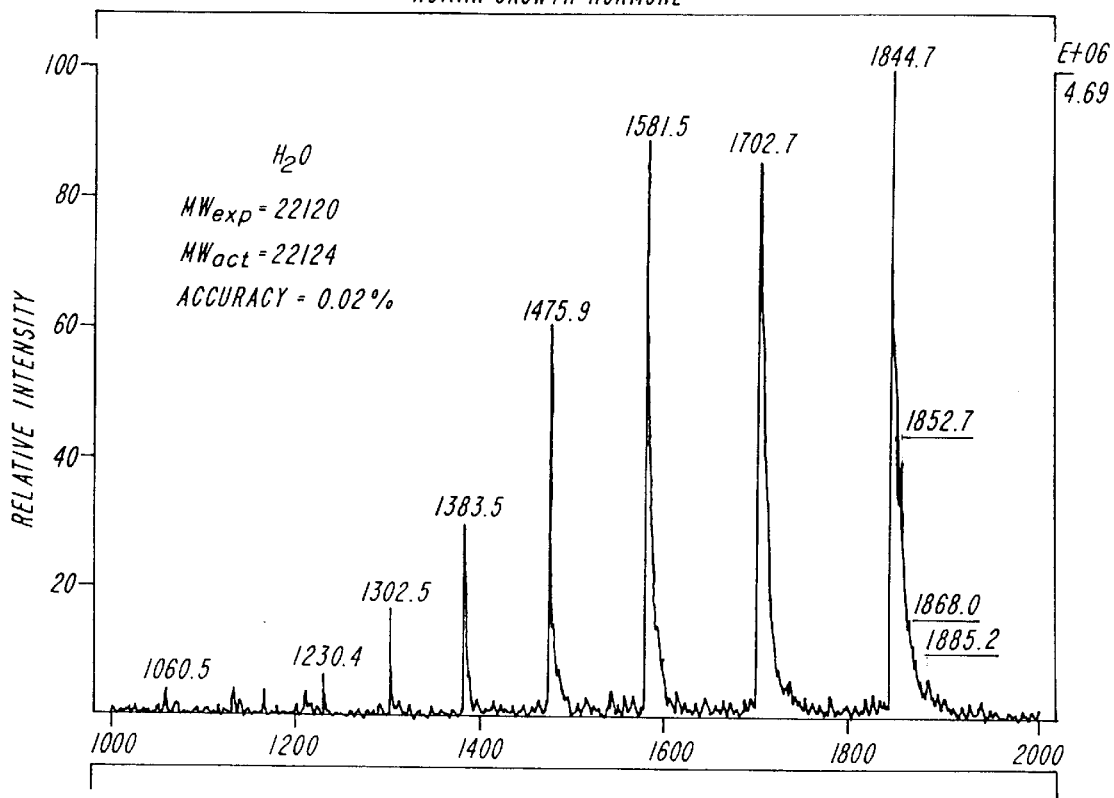
FIG. 11A  H₂O VS. 75% MeOH HUMAN GROWTH HORMONE
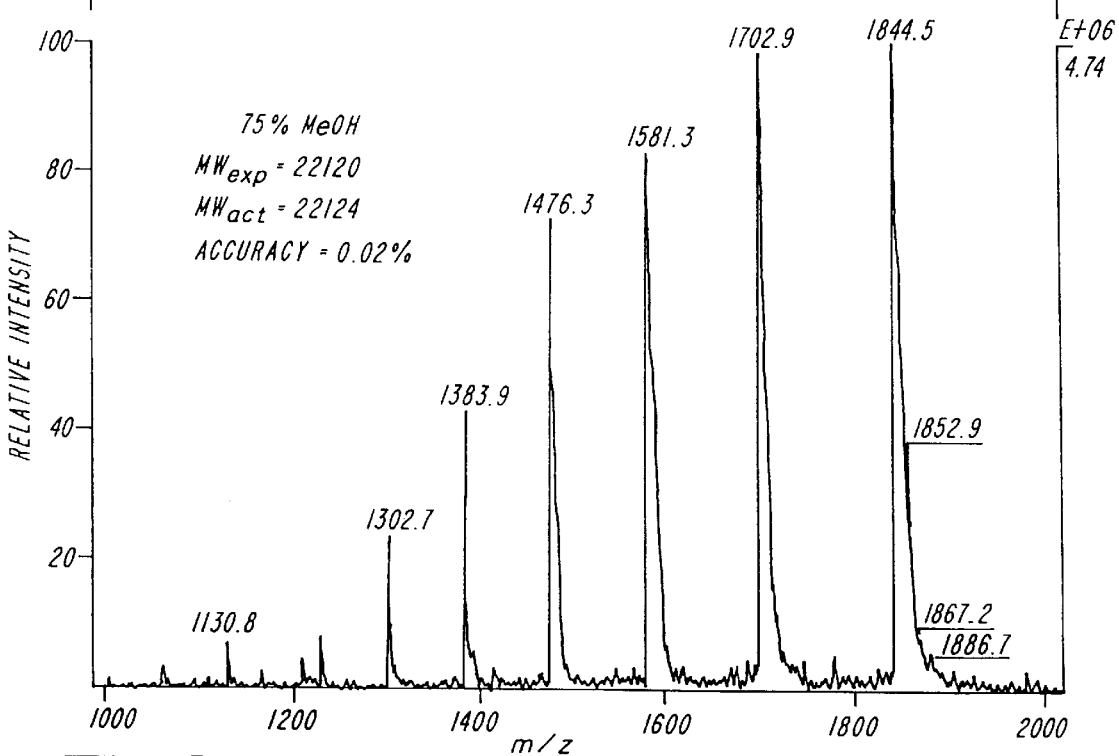
FIG. 11B

MICROSCALE FLUID HANDLING SYSTEM

This application claims benefit of U.S. Provisional Application No. 60/001,349, filed Jul. 21, 1995.

FIELD OF THE INVENTION

This invention relates to microscale fluid handling systems and particularly to such systems fabricated in a microscale device.

BACKGROUND OF THE INVENTION

Recent developments in microfabrication techniques have permitted the integration of microminiature tools for biochemical analysis within a tiny device. Complete chemical processing systems, e.g., reaction chambers, separation capillaries and their associated electrode reservoirs, as well as certain types of detectors, can be consolidated on a microchip of, e.g., a glass or fused silica. Such "laboratories-on-a-chip," in principle, permit effective utilization and manipulation of minute quantities of material. After the intended procedures have been conducted, the processed compounds are available on the chip in a spatially concentrated form that is suitable for performing further analytical operations. As the sample components are in volumes on the order of nanoliters, subsequent operations should preferably be carried out on the same device. (See, e.g, Effenhauser et al., Anal. Chem. 67:2284–2287, 1995.) This constraint, however, permits less than efficient utilization of certain powerful analytical instruments, such as a mass spectrometer.

SUMMARY OF THE INVENTION

The invention is directed to a microscale fluid handling system that permits the efficient transfer of nanoliter quantities or other small quantities of a fluid sample from the spatially concentrated environment of a microscale device, such as a microfabricated chip, to "off-chip" analytical or collection devices without an increase in sample volume. The fluid handling system of the invention is fabricated in the form of one or more capillary channels in a body or substrate, which may be made of a suitable non-conductive material, such as silica or polymer plastic, or a suitable conductive material such as stainless steel, noble metal, or semi-conductive material such as silicon. The microscale device of the invention includes one or more exit ports integral with an end of one or more of the channels for consecutive or simultaneous off-chip analysis or collection of an applied sample. The exit port or ports may be configured, for example, to transfer a sample for electrospray-mass spectrometry analysis (ESI/MS), for atmospheric pressure-chemical ionization mass spectrometry analysis (APCI/MS), for matrix assisted laser desorption ionization mass spectrometry (MALDI/MS), for nuclear magnetic resonance analysis (NMR), for pneumatically or ultrasonically assisted spray sample handling, for transfer to an off-chip detection system, such as electrochemistry, conductivity or laser induced fluorescence, or for collection of specific fractions, e.g., in collection capillaries or on collection membranes. Sample transfer may be by droplet, spray or stream, as desired, or as suitable for the instrument or device receiving the transferred sample. The transferred fluid may be in the form of a liquid or a gas.

The channels of the microdevice may be arrayed in any format that allows for sequential or simultaneous processing of liquid samples. In one embodiment of the invention, the channels are arranged in spaced parallel form, each channel representing an independent microanalytical system having its own sample introduction port and exit port. In another embodiment, the channels on the microscale device are arranged in a circular pattern, like the spokes of a wheel. At the center of the circular pattern, all channels can converge into one exit port integrally formed in a face of the microscale device. The exit port is adapted to interface with an external device, such as a mass spectrometer or membrane, which receives samples via the exit port for analysis.

In any embodiment, each channel may include electrical contacts, so that an electric circuit path can be established along the channel. For example, one electrical contact can be on the entrance side of a channel and another electrical contact can be on the exit side. In an alternative arrangement, an electric circuit can be completed by an external contact, beyond the exit end of the channel. For example, if the exit port of a channel is used as an electrospray source for a mass spectrometer, the mass spectrometer sampling orifice can serve as the counter electrode. Samples can be transferred off chip for subsequent analysis by switching the electric current sequentially to each channel on the chip. At the end of the analysis, the chip may be discarded. Thus, the invention alleviates manipulations such as flushing and eliminates problems of sample carryover between runs while providing for efficient use of the mass spectrometer or other device for analysis and/or collection.

Samples can be introduced into a channel on the microscale device of the invention by a variety of methods, e.g., by pressure, electrokinetic injection, or other technique, and an electrical current and/or pressure drop can then be applied to cause the sample components to migrate along the channel. The channels may function only for fluid transfer, e.g., to a mass spectrometer, or the channels can serve as environments for various types of sample manipulations, e.g., for micropreparative or analytical operations, such as capillary electrophoresis (CE) or the polymerase chain reaction (PCR), or for carrying out any type of sample chemistry. The channels may be filled with membrane or packing material to effectuate preconcentration or enrichment of samples or for other treatment steps, such as desalting. Furthermore, other modification of sample components, e.g., by enzymes that are covalently bound to the walls of a channel or are free in a channel, are possible. Packing material may be bound to the walls of the channels or may include other components, such as magnetic particles, so that when a magnetic field is applied, the magnetic particles retain the packing material in place. The magnetic particles can also be used for efficient mixing of fluids inside the channels, using an external magnetic field. A micromachined filter or other stationary structure may also be employed to hold packing material in place. Alternatively, stationary structures can be micromachined, cast or otherwise formed in the surface of a channel to provide a high surface area which can substitute for packing material. Another method of applying samples is to attach a miniaturized multiple-sample holder as a hybrid micromachined system to the entrance ports of the channels.

A sample can be introduced into a channel in a short starting zone or can fill the whole channel completely. Filling only a small part of the channel with the sample is preferable when an on-chip separation of sample components is to be carried out, such as electrophoresis or chromatography. Filling the whole channel with the sample may be advantageous in cases when off-chip analysis requires extended sample outflow, such as sample infusion/electrospray ionization for structure analysis by mass spectrometry.

In many cases a liquid flow may be required to transport the analytes in a sample into a specific channel, or along the length of the channel, or out of the channel via an exit port. Therefore, to assist in the required fluid transfer, a pumping device may be incorporated into or associated with the microscale device of the invention. For example, a heating element can be used to cause thermal expansion, which will effectuate sample liquid movement, or a heating element can be used to generate a micro bubble, the expansion of which causes the sample to travel in the channel. Other options may include pumping by the pressure of a gas or gases generated by on-chip electrolysis. Flow can be also generated by application of a pressure drop along a channel or by electroosmosis inside a channel.

As samples move to the end of a channel, they can be subjected to detection or analysis at a site external to the microscale device of the invention by a variety of techniques, including mass spectroscopy, nuclear magnetic resonance, laser induced fluorescence, ultraviolet detection, electrochemical detection, or the like. The end of each channel may include a tip configured to facilitate transfer of the sample volume. When mass spectroscopy is the analytical method, the end of each channel may be microfabricated to form an electrospray exit port, or tip, that permits transfer of ions into the sampling orifice of the mass spectrometer by microelectrospray. Other exit port configurations can be used for, pneumatically or ultrasonically assisted spray sample transfer, among others. Furthermore, if the sample to be transferred is a dissolved gas, transported in the channel by a carrier liquid, the exit port can be configured to heat the carrier liquid, to restore the sample to the gas phase for spray transfer.

The exit end of the channel may be configured and/or sized to serve as an electrospray tip, or the tip can be formed as an extension of the channel or as an attachment to the channel. The edge surface of the substrate may be recessed between adjacent exit ports to minimize cross-contamination, or the substrate may be of a non-wetting material, or may be chemically modified to be non-wetting, so that the exiting liquid itself provides the electrospray. When necessary, the microdevice can be positioned on a translational stage so that each exit port can be precisely aligned, in turn, with the sampling orifice of the mass spectrometer or other utilization device.

The invention may be used in a fluid sheath (e.g., liquid or gas) or sheathless mode depending on the type of analysis required and the size of the sample exiting a channel. In a sheathless arrangement, the exit port is formed at the end of the channel. When a liquid sheath is required (e.g., for the addition of a liquid, a chemical and/or a standard prior to electrospray or to provide electric connection via the sheath fluid), an exit port can be created at the merge point of two channels, one supplying the sample and the other the sheath liquid. Selective analysis of analytes in both the cationic and anionic modes can be performed easily by rapid switching of the polarity of the electric field.

Different sized channels may be employed on the same microscale device. For example, larger channels may be used for cleanup operations, and smaller channels may be used for processing operations. Moreover, other operations can be performed in other regions of the device, such as chemical processing, separation, isolation or detection of a sample or a component of the sample, prior to sample loading in a channel. Thus, it is possible to carry out sample chemistries or to conduct micropreparative and analytical operations on both a starting sample and its separated components within the device of the invention, prior to transfer of the sample or its components off chip for further analysis or collection. Additionally, detection of a sample may be carried out on the microdevice itself, e.g., by a fiber optic detection system, which can provide complementary control information for off-chip analysis and detection, or by any other suitable detector such as laser induced fluorescence, conductivity and/or electrochemical detector.

Suitable processes for fabricating the microscale device of the invention are themselves well known in the art and include, as examples, photolithographic and etching techniques, laser machining, multilayer fabrication techniques such as stereolithography, and stamping, molding or casting techniques.

The channels may be cylindrical, trapezoidal or of any other cross-sectional shape. The channel pattern may be linear or curvelinear within a single plane. Furthermore, the microdevice may include multiple such layers of independent, unconnected channels. Alternatively, an individual channel may extend between two or more planes to enable transfer of a sample from a desired entrance port location to a desired exit port location. A channel also may be of any length necessary to enable such a transfer. At its most basic, a channel may be merely a straight slit connecting an inlet port and an exit port.

Buffer reservoirs, reaction chambers, sample reservoirs, and detection cells may also be fabricated along with each individual channel. More complex structures can be created by stacking or otherwise assembling two or more microfabricated devices. In addition, individual instrument blocks such as sample reservoirs, pretreatment or separation channels, and exit ports can be micromachined separately and combined into one complete system in much the same way as hybrid integrated circuits in electronics are formed. Microfabrication techniques are precise and will allow for a high degree of reproducibility of selected channel and exit port shapes and dimensions.

The microscale fluid handling system of the invention permits more efficient use of powerful analytical devices, such as the mass spectrometer, than is currently possible. In addition, the system of the invention can be manufactured as a disposable device that is suitable for cost effective automation of the analysis of a large number of samples. Using this micromachined approach, high throughput analysis by mass spectrometry would be possible. In addition, handling of small volumes and quantities of samples would be facilitated, and consumption of valuable samples and reagents would be reduced. Applications include any laboratory analysis methods, especially where high throughput and minimization of cross-contamination are desirable, such as screening and diagnostic methods, and such other analytic methods as pharmacokinetics where fresh columns are required for each run.

Other features and advantages of the invention will be apparent from the following description of the preferred embodiments thereof and from the claims.

BRIEF DESCRIPTION OF THE DRAWINGS

FIGS. 2b–2d are side views of three different embodiments of the exit port depicted in FIG. 2a;

FIG. 6a is a schematic representation of the microscale device of FIG. 1a used as an electrospray interface with a mass spectrometer;

FIG. 6b is an enlargement of an indicated portion of FIG. 6a;

FIGS. 8a–8d show electrospray mass spectra from infusing different samples in methanol/water/acetic acid (75/25/0.1) from different channels of the microscale device of: FIG. 8a, 0.1 mg/ml myoglobulin; FIG. 8b, 0.1 mg/ml endorphin; FIG. 8c, 0.1 mg/ml human growth hormone; and FIG. 8d, 0.1 mg/ml ubiquitin;

FIG. 11a shows an electrospray mass spectrum from infusing 0.05 mg/ml human growth hormone from aqueous solution, with methanol/water/acetic acid (75/25/0.1) in a syringe for applying pressure, and FIG. 11b shows an electrospray mass spectrum from infusing 0.05 mg/ml human growth hormone directly from a solution of methanol/water/acetic acid (75/25/0.1);

DETAILED DESCRIPTION OF THE INVENTION

Figure 1A:
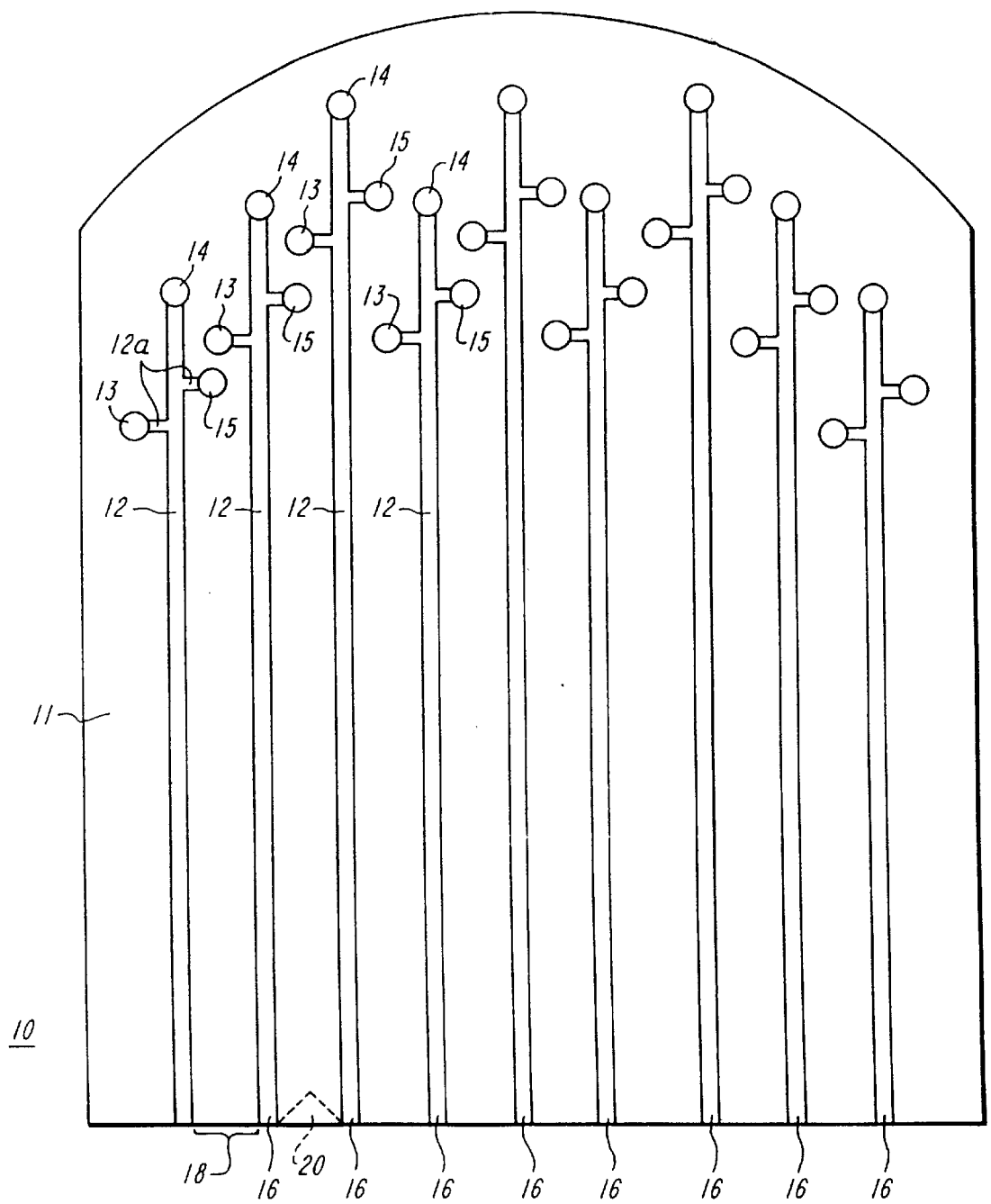
FIG. 1a is a plan view of one embodiment of the microscale fluid handling system of the invention, in which the associated channels for sample transport are in a parallel arrangement within a single plane.
Figure 1B:
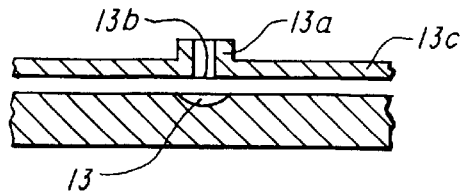
FIG. 1b is a cutaway view of an embodiment of the invention showing optional well extensions.

The microdevice of the invention permits the integration of microscale reaction and separation systems with the powerful analytical and/or collection systems that are only available off-chip. One embodiment of the invention is shown in FIGS. 1a and 1b and includes a microchip substrate or body containing a series of independent channels or grooves, fabricated in a parallel arrangement along with their associated sample inlet ports and buffer reservoirs, in one surface of a planar portion of a glass body or chip. Exit ports are fabricated at the end of their respective channels, on the edge of the chip. The grooved portion of the chip is covered with a cover plate to enclose the channels.

Referring to FIG. 1a, the chip (10), shown without its associated cover plate, contains nine parallel channels (12), all of the same width and depth (60 $\mu$m×25 $\mu$m), etched in a surface of the microchip substrate (11). The channels are of three different lengths in order to optimize the channel arrangement. Each channel (12) is connected to three wells (13, 14, 15) which allow access to the channels, e.g., for infusing samples through the channels, for manipulating different solutions that might be added to a sample in a channel, and also for use as an electrophoresis buffer reservoir. Each well has a diameter of 1 mm and a depth of 0.5 mm, with a volume of 0.4 $\mu$L. Each well (13 and 15) is coupled to its corresponding channel by a groove or channel (12a). Plastic microtubes (not shown) can be attached on top of the cover and in communication with the wells to increase their volume, for example, up to 10 $\mu$L. Referring to FIG. 1b, samples are introduced into wells (13), through optional well extensions (13a) and sample entrance holes (13b) in cover plate (13c), by any convenient means such as supply tubes or syringes at which the chip is placed during sample loading.

Referring again to FIG. 1a, exit ports (16) at the end of each channel, and at the edge of the microchip substrate, serve as electrospray exit ports through the use of a non-wetting coating, e.g., polydimethylsiloxanediol, on the external surface area (18) of the microchip substrate between two exit ports (16), to isolate a solution to be electrosprayed from an exit port. The channels are spaced from each other in the illustrated version by 6 mm. Alternatively, indentations or recesses (20) can be cut in the external surface of the microchip substrate between adjacent exit ports (16), to isolate the exit ports and avoid or minimize cross-contamination between channels.

Figure 1C:
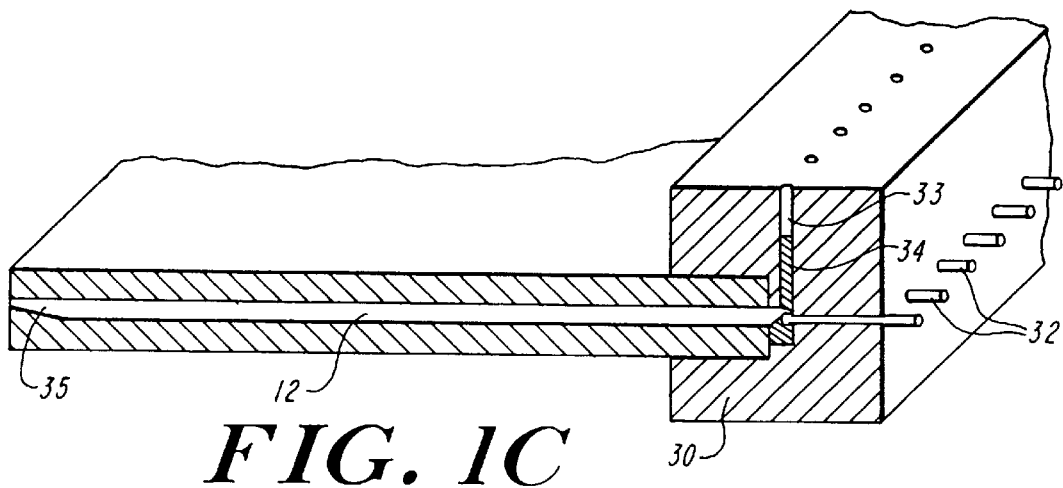
FIG. 1c is a cutaway view of an embodiment of the invention showing an attached sample/electrode port block.

In the embodiment of the invention shown in FIG. 1c, a sample/electrode port block is provided as a separate element which is attached to the microchip body. Referring to FIG. 1c, the body (11) has a sample/electrode port block (30) disposed along one side of the body. The block (30) contains sample inlet ports (31) which are coupled via supply channels (33) to the inlet end of respective channels (12). An electrode (32) is supported by the block (30) and has one end disposed in the supply channel (33) and the opposite end external to the block for connection to a high voltage power supply. In this embodiment, the supply channel (33) contains a packing material (34) for internal sample pretreatment. The illustrated channel (12) has a tapered end (35) forming an exit port tip from which the sample liquid is sprayed for transfer to an external collection or analytical device.

Figure 1D:
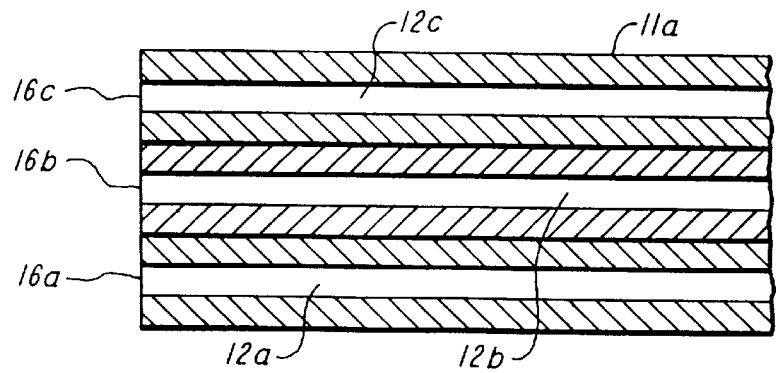
FIG. 1d is a cutaway view of an embodiment of the invention showing multiple layers of unconnected channels for sample transport.

For certain applications, the microdevice substrate is fabricated to contain multiple layers of independent, unconnected channels. Referring to FIG. 1d, a cutaway view of an embodiment of the invention shows independent channels (12b), (12c) and (12d) each representing multiple channels within a single plane according to the embodiment of the invention shown in FIG. 1a. The planes containing channels (12b), (12c) and (12d) are positioned in multiple stacked layers, one above the other, in substrate block (11a), with each channel in each layer ending in its own exit port, represented by exit ports (16b), (16c) and (16d), respectively, as shown. This embodiment is particularly useful for high throughput screening of multiple samples.

Figure 1E:
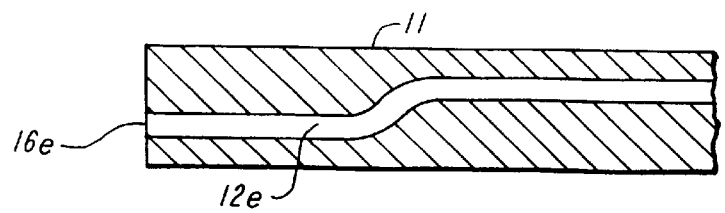
FIG. 1e is a cutaway view of an embodiment of the invention showing a channel in multiplane configuration.

In the embodiments described above, the channels lie generally within a single plane of the substrate or body. The channels may also extend between two or more planes such as shown in FIG. 1e. As illustrated, the channel (12e) extends from a first upper plane to a second lower plane and ends in exit port (16e) at the edge of the microchip substrate (11). In general, the channels can be of any configuration and follow any convenient path within the substrate or body (11) in order to permit intended packing density of the channels and associated components of the microchip device.

The distance between two given channels is chosen depending on the required density of the channels and on the associated chemistries as well as to minimize cross-contamination. If a low channel density is desired, the distance between individual channels (and between individual exit ports) can be several millimeters. In this case, the entire device can be positioned on a moving stage for precise alignment of each exit port with an off-chip (off-microdevice) analyzer. If a high channel density is desired, the channels and their associated exit ports will be closer together (separated only by several tens of microns). In this case, a moving stage may not be necessary.

Figure 2A:
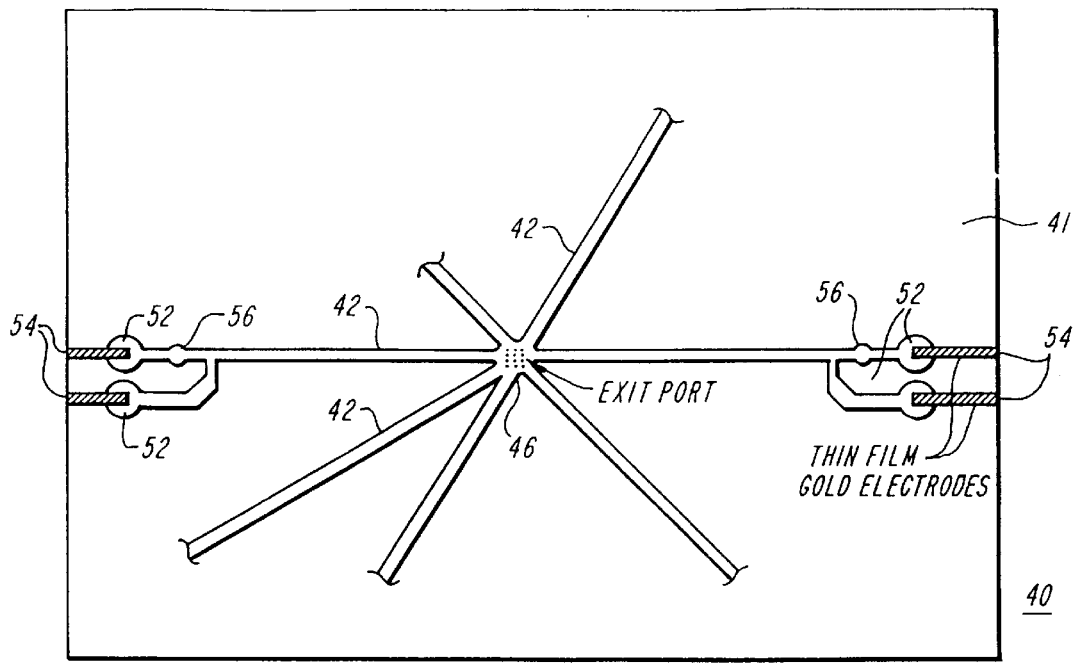
FIG. 2a is a plan view of another embodiment of the microscale fluid handling system of the invention in which the associated channels for sample transport are in a circular arrangement, merging in a common exit port.

The invention can also be implemented with the channels in a circular or spoke arrangement. Referring to FIG. 2a, an array of capillary channels (42) is provided in the body (40) in a circular or spoke arrangement. The inner ends of the channels (42) confront a common exit port (46). The inlet ends of the channels are coupled to a sample inlet (56) and buffer reservoirs (52) as illustrated. Electrodes, typically of thin film gold, formed on or attached to the substrate (41), each have an end disposed within a respective buffer reservoir and an opposite end accessible for connection to an external power supply. The sample inlets (56) and buffer reservoirs (52) are accessible for supply of liquids, or for associated ports and/or tubes extending to a surface of the substrate or outwardly therefrom for coupling to supply apparatus.

Figure 2C:
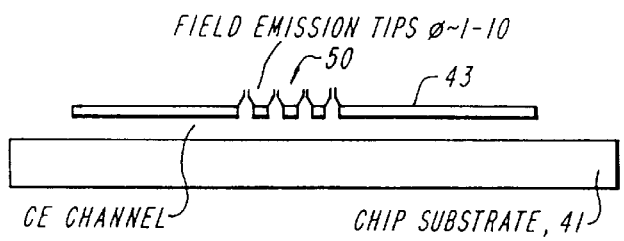
Figure 2B:
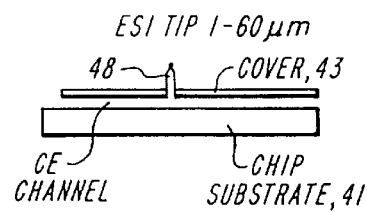
Figure 2D:
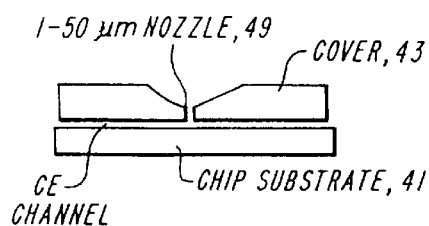

The exit port may be of various configurations. Referring to FIG. 2b, the exit port is shown coupled to an electrospray tip (48) extending outwardly from a cover plate (43), which encloses the channels of the substrate. The tip typically has an exit orifice of about 1 to 60 micrometers. In the embodiment of FIG. 2c, the exit port (46) is coupled to an array of field emission tips (50), each having an exit orifice of about 1 to 10 micrometers in diameter. A further alternative exit port configuration is shown in FIG. 2d in which a nozzle orifice is formed within a recess (49) in the cover plate (43) adjacent exit port (46). The nozzle orifice is of about 1 to 50 micrometers in diameter.

Figure 3:
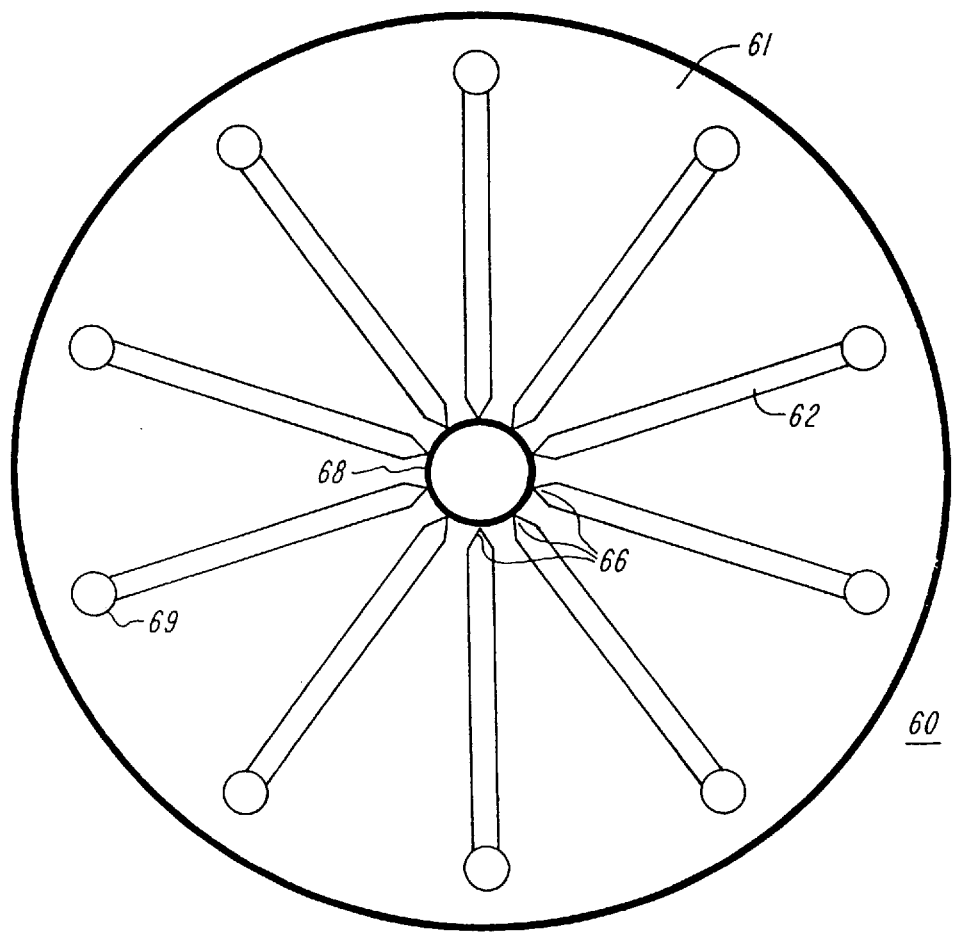
FIG. 3 shows another circular arrangement of sample transport channels in which each channel ends in a separate exit port on the rim of a hole in the center of the chip.

In a further embodiment shown in FIG. 3, the channels (62) are arranged in a regularly spaced circular array in substrate (61). The outer ends of the channels (62) join respective reservoirs (69). An electrode is provided for each reservoir (69) as in the embodiment described above. Each of the channels has an inner end tapering to an individual exit port (66), all of which are accessible through a single hole (68) in the substrate (61) in the center of the array. The channels may each contain one or more sample reservoirs and one or more buffer reservoirs to suit intended performance and operational requirements.

Figure 4:
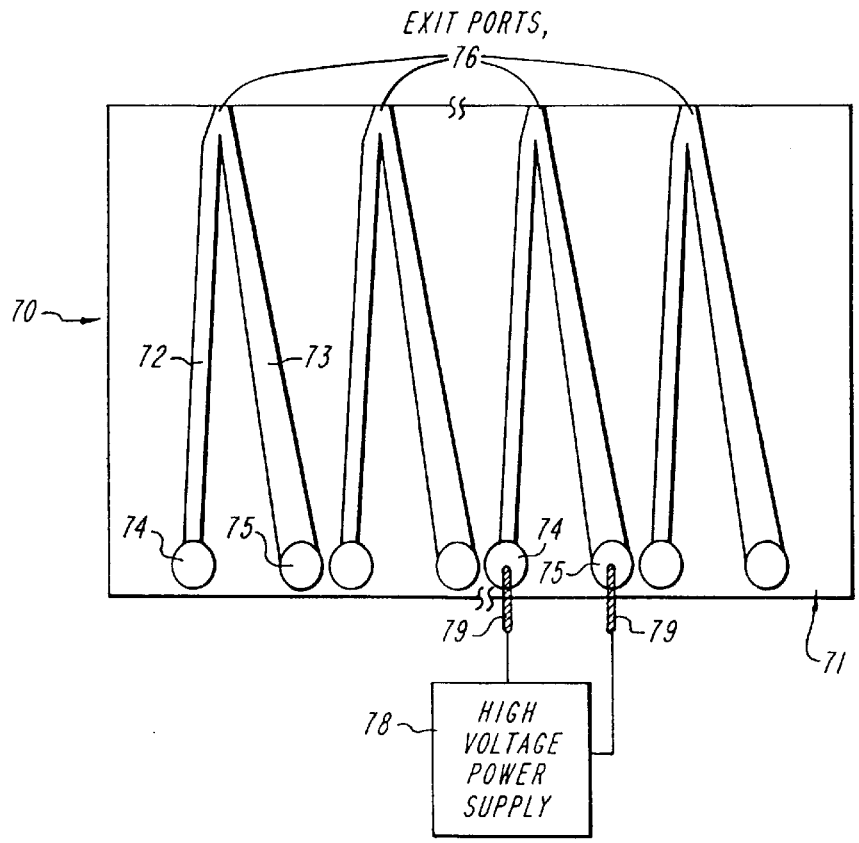
FIG. 4 is a plan view of an arrangement of channels in another embodiment of the invention in which the exit ports are configured as spray ports, to be used with a sheath liquid for either pneumatic spray or electrospray for off-chip sample manipulation.

FIG. 4 shows an embodiment having pairs of sample separation/infusion channels (72) and sheath (reagent) liquid channels (73), each pair converging in an exit port (76). The exit ports are spray ports, to be used with a sheath liquid or gas. Either pneumatic spray or electrospray can be carried out for off-chip sample analysis or collection. For electrospray transfer of a sample in the sheath mode, a high voltage power supply (78) is connected between electrodes (79) in a sample reservoir (74) and in a sheath reservoir (75). Alternatively, the voltage can be applied between an electrode in reservoir (74) or (75) and an electrode at the entrance of a mass spectrometer adjacent to the exit ports (76). In the first arrangement, the electrospray potential at the exit ports (76) is a function of the total applied voltage and the resistances of both channels (72) and (73). In the second arrangement, the electrospray potential at the exit ports (76) is directly proportional to the voltage applied at the sample reservoir. The exit ports may also contain an electrode for active control of their potential.

The sheath liquid flow can be controlled in the same way as described earlier for flow in the sample channels. The sheath liquid composition depends on the desired application. For example, the liquid can contain a water/organic solution of a volatile acid(or base) to control the pH of the electrosprayed solution. The sheath liquid can also contain a solution of a suitable matrix (e.g., dihydrobenzoic acid, sinapinic acid) for matrix assisted laser desorption and consecutive time of flight (TOF) mass spectrometric analysis. Both electrospray and pneumatic assisted spray can be used in this case. Laser and/or matrix assisted laser desorption ionization can be performed after deposition of the solution exiting the microdevice on an external support, e.g., membrane, stainless steel, etc.

Figure 5:
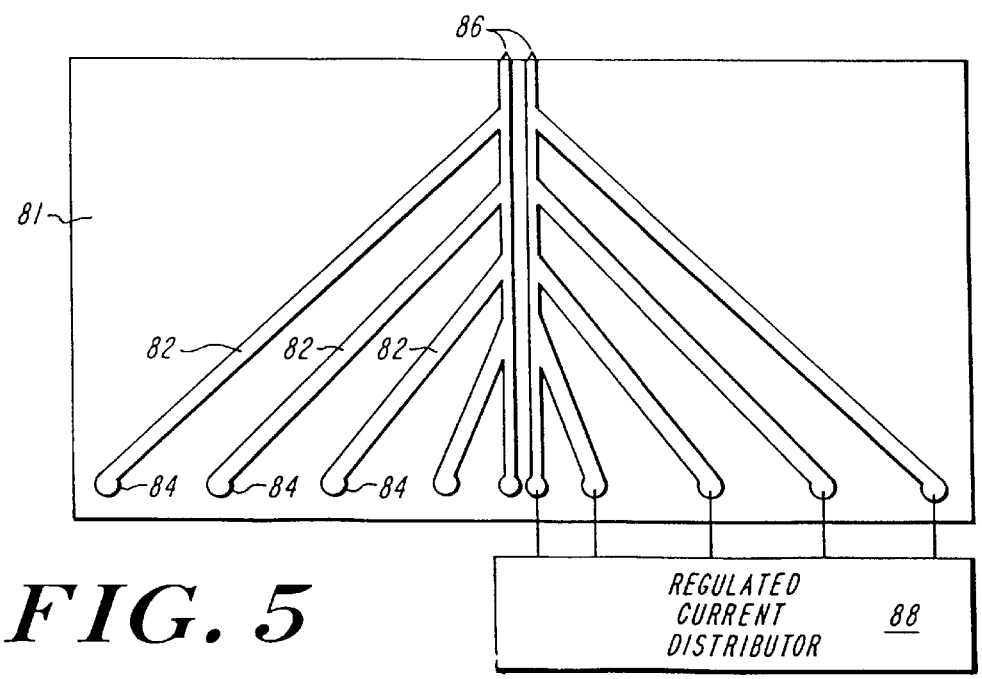
FIG. 5 is a plan view of an arrangement of channels in another embodiment of the invention in which several channels merge into one exit port.

FIG. 5 shows an embodiment in which a substrate has several inlet ports (84) and channels (82) merging in one exit port (86). Two such arrays are shown in FIG. 5. Each channel (82) can be supplied with different fluids containing, for example, a calibrating standard, liquid sheath fluid or a chemical reagent to improve off-chip analysis. The flow in each channel can be pressure controlled, or a regulated electric current distributor (88) can be used for precise control of electromigration and electroosmosis in the channels.

As described above, the microchip device of the invention can be used as an electrospray interface for transfer of a sample to a mass spectrometer (ESI/MS). Referring to FIG. 6a, to increase sample injection efficiency for detection in the mass spectrometer, the microchip (10) of FIG. 1a is mounted on a three-dimensional stage (21), which allows precise alignment, as shown in FIG. 6b, of a channel exit port (16) with the sampling orifice (22) of the mass spectrometer (23). One well (14) coupled to a channel (12) is used as an electrophoresis buffer reservoir. Another well (13) is used for sample input. A third available well (15) is plugged and not used in this embodiment. When a sample infusion experiment is carried out, the wells are made airtight, e.g., through the use of plastic stoppers, so that pressure can be applied for transport of a fluid sample in a channel towards the respective channel exit port.

A low current, high voltage power supply (24) is used to apply a voltage via an electrode (25) inserted in a buffer reservoir well (14) to each channel (12) in turn, for electrospray transfer of a sample in the respective channel. The high voltage power supply (24) is grounded (26) and there is a second ground (27) on the mass spectrometer. The largest portion of the voltage potential is across the gap between the electrospray exit port (16) and the mass spectrometer sampling orifice (22), thus causing electrospray transfer of the sample to take place. The electrospray transfer of fluid samples from the nine channels of the microchip is carried out in a sequential mode. While one channel is used for injecting a sample into the mass spectrometer, another channel can be used for sample preparation. After each mass spectrometer analysis, the next channel will be moved by stage (21) to align with the sampling orifice. The alignment can be performed manually, by adjusting the position of the three-dimensional stage by hand, or automatically, by moving the stage with a stepper motor. Once an optimized voltage is reached, determined, e.g., by increasing the voltage until the best signal is obtained, it can be used for the next channel without further adjustment. The distance between the exit ports and the sampling orifice of the mass spectrometer is not critical and can be in the range of less than a millimeter to several tens of millimeters.

The following examples are presented to illustrate the advantages of the present invention. These examples are not intended in any way otherwise to limit the scope of the invention.

EXAMPLE I

Infusing the same sample from different channels

Figure 7A:
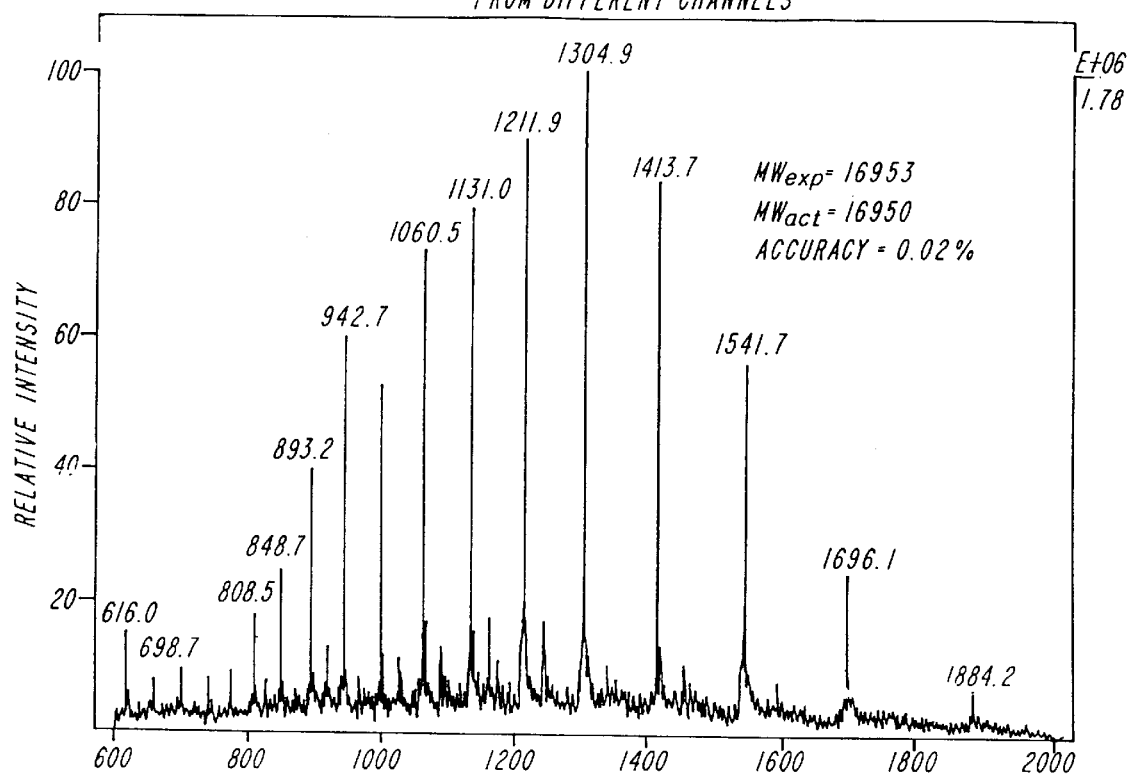
FIGS. 7a and 7b show electrospray mass spectra from infusing 0.01 mg/ml myoglobin (200 nl/min) from two selected channels of the microscale device of FIG. 1a, of the same width and depth.
Figure 7B:
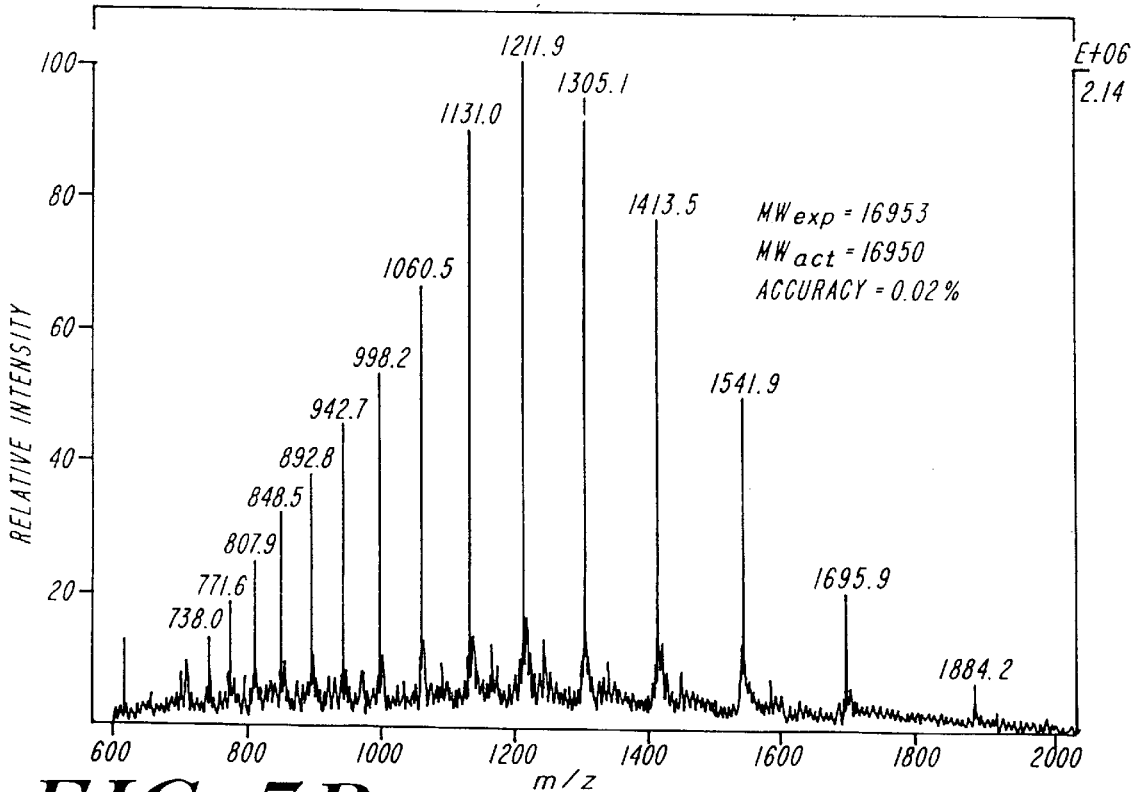

To investigate the performance of different channels, a 0.01 mg/ml myoglobin sample was infused from two selected channels of the same cross-section, using the embodiment of the microdevice of the invention shown in FIG. 1a. As shown in FIGS. 7a and 7b, the sensitivity of the recorded electrospray mass spectra was very similar for these two channels, implying that the microfabrication process used to prepare the microdevice of the invention can generate reproducible channels. The experimentally determined molecular weight of myoglobin was 16,953, which, when compared to the actual molecular weight of 16,950, represents an accuracy limit of 0.02%. The subtle differences in the spectra are typical for analyzing proteins.

EXAMPLE II

Figure 8A:
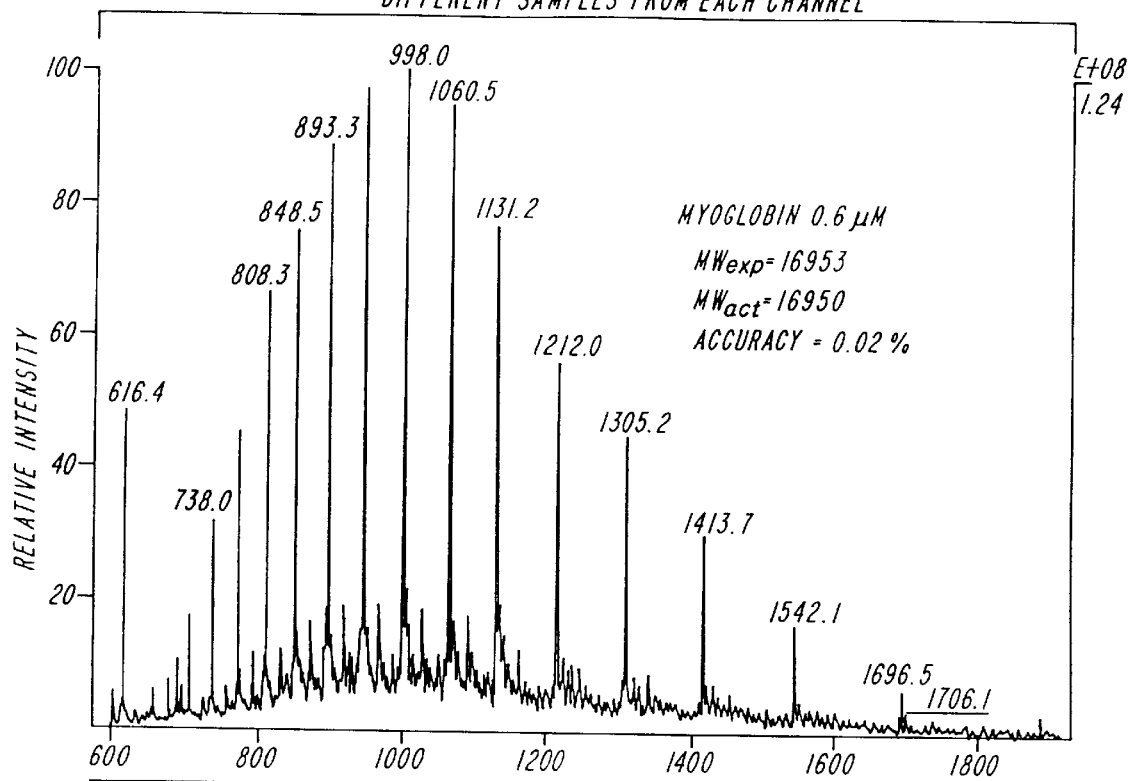
Figure 8B:
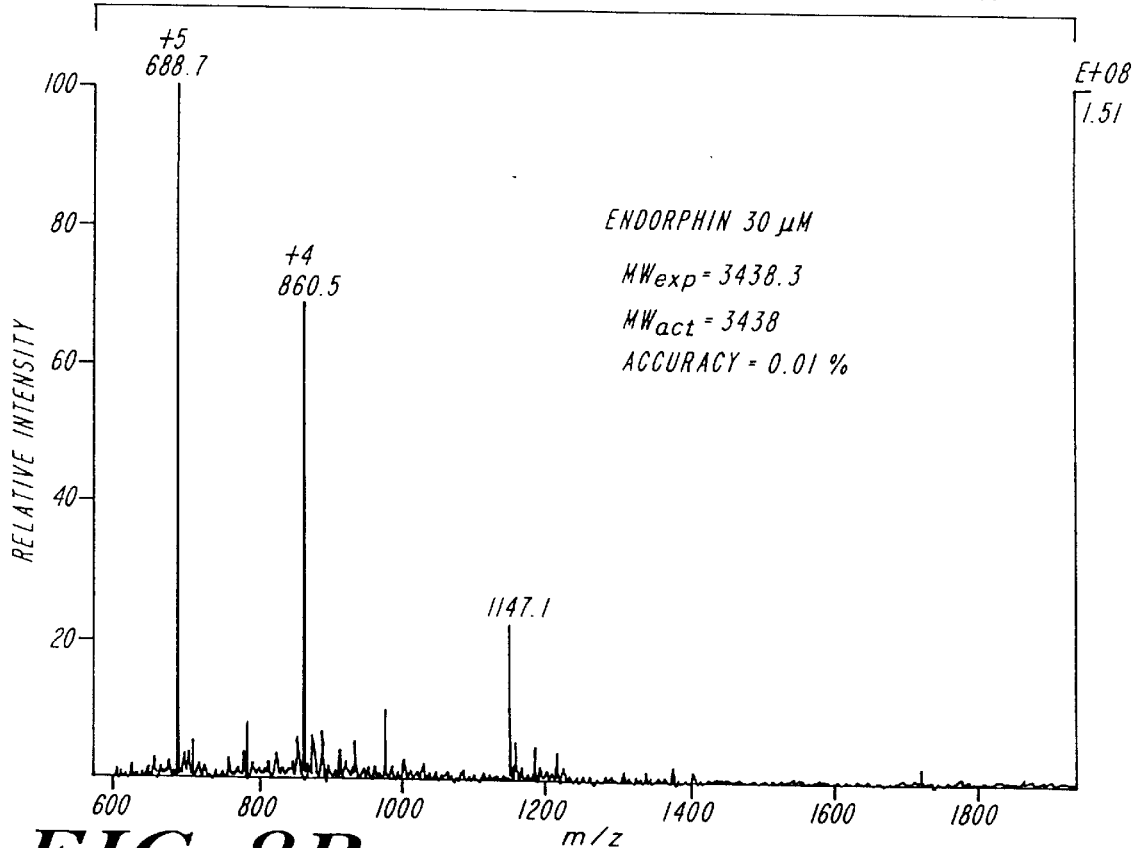
Figure 8C:
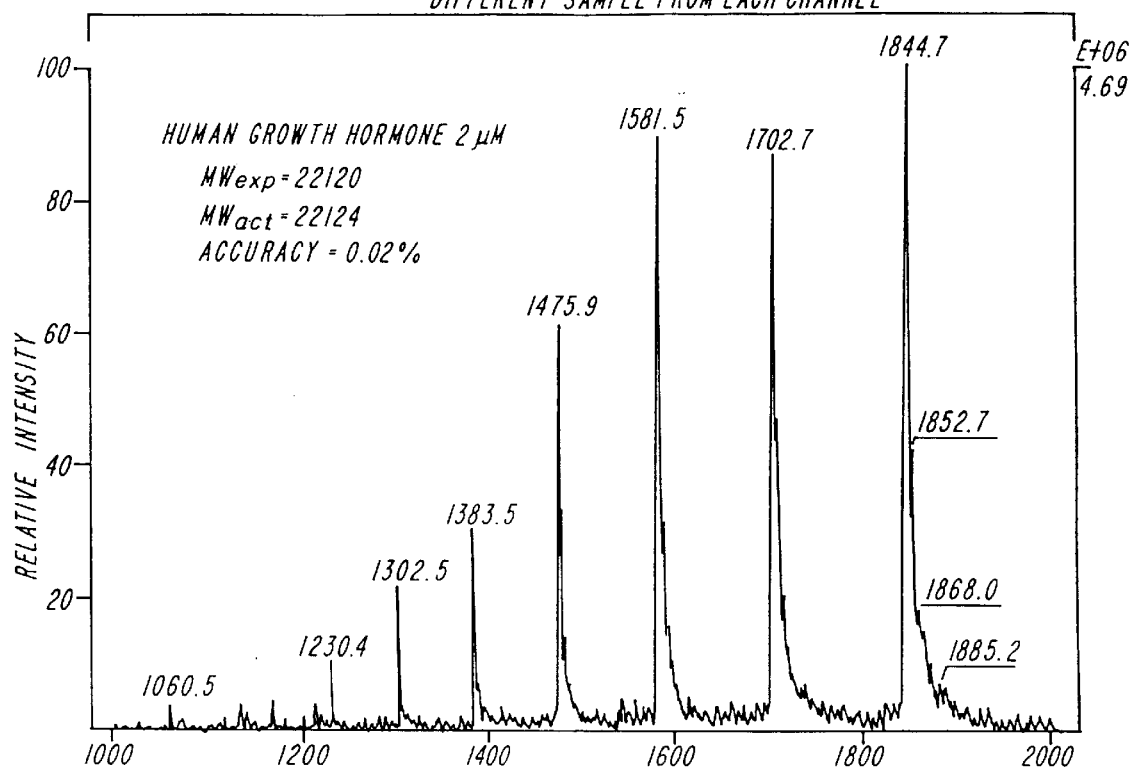
Figure 8D:
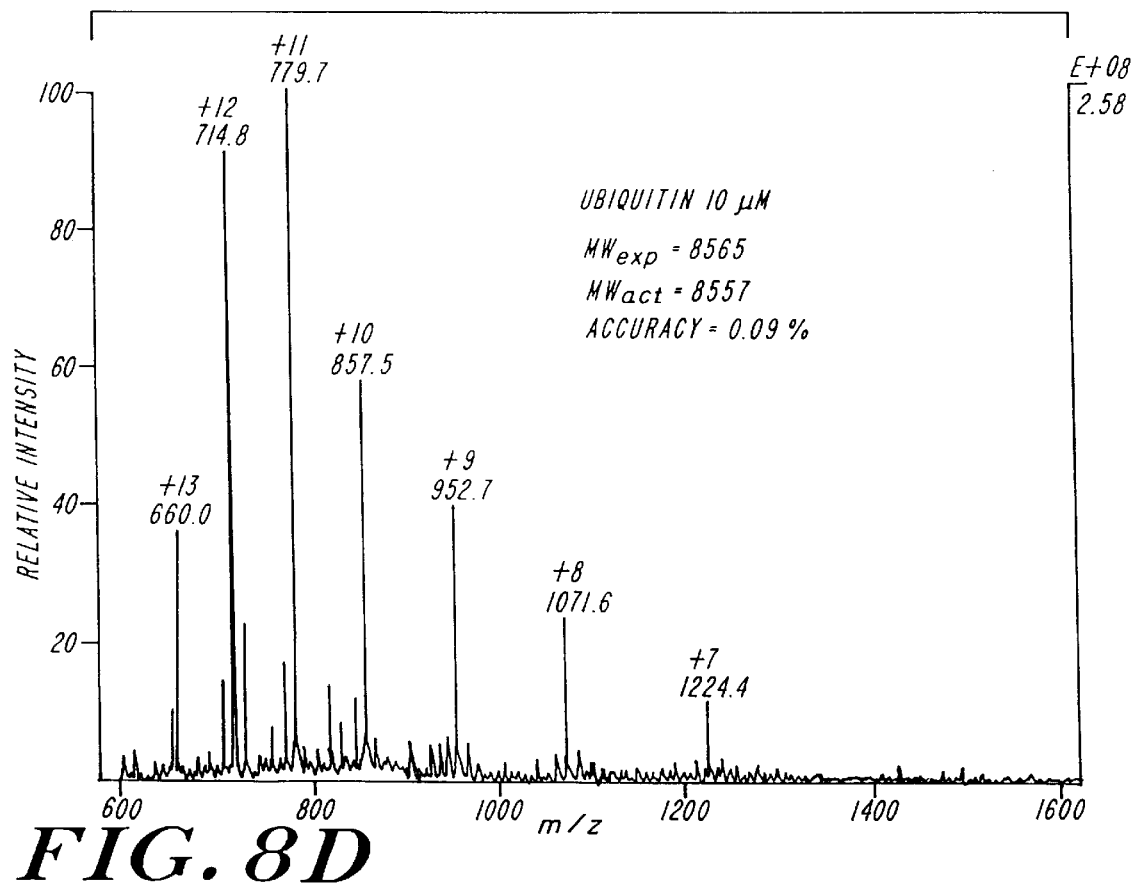

Infusing different samples from different channels for conducting high-throughput analysis To demonstrate that the microchip of the invention can be used as an electrospray interface with a mass spectrometer for sequential analysis, four different sample were processed in sequence, with each sample (in methanol/water/acetic acid; 75/25/0.1) being sprayed from a different channel on the microdevice shown in FIG. 1a. Spectra corresponding to the four analyzed examples are presented in FIGS. 8a–8d. The experimentally determined molecular weight, the actual molecular weight and the accuracy limit for each sample were as follows: FIG. 8a, 0.1 mg/ml myoglobulin, $MW_{exp}$=16,953, $MW_{act}$=16,950, accuracy limit=0.02%; FIG. 8b, 0.1 mg/ml endorphin, $MW_{exp}$=3438.3, $MW_{act}$=3438, accuracy limit=0.01%; FIG. 8c, 0.1 mg/ml human growth hormone, $MW_{exp}$=22,120, $MW_{act}$=22124, accuracy limit=0.02%; and FIG. 8d, 0.1 mg/ml ubiquitin, $MW_{exp}$=8565, $MW_{act}$=8557, accuracy limit=0.09%. Each analysis can be carried out in a few minutes when the system is operated in a sequential analysis mode, a very high throughput for analyzing biological samples. This operational approach implies that sample preparation can be conducted in one channel while another channel is being used simultaneously to analyze a sample. In this mode, the utilization efficiency of the mass spectrometer will be higher than has been possible before. With a similar design to that shown in FIG. 1a, a microdevice of the invention with as many as 20 channels can be fabricated for increasing the analysis throughput of a mass spectrometer. Furthermore, a microdevice having a three-dimensional array of channels, such as is shown in FIG. 1d, would make even a substantially higher sample throughput possible.

EXAMPLE III

Study of detection limit

Figure 9:
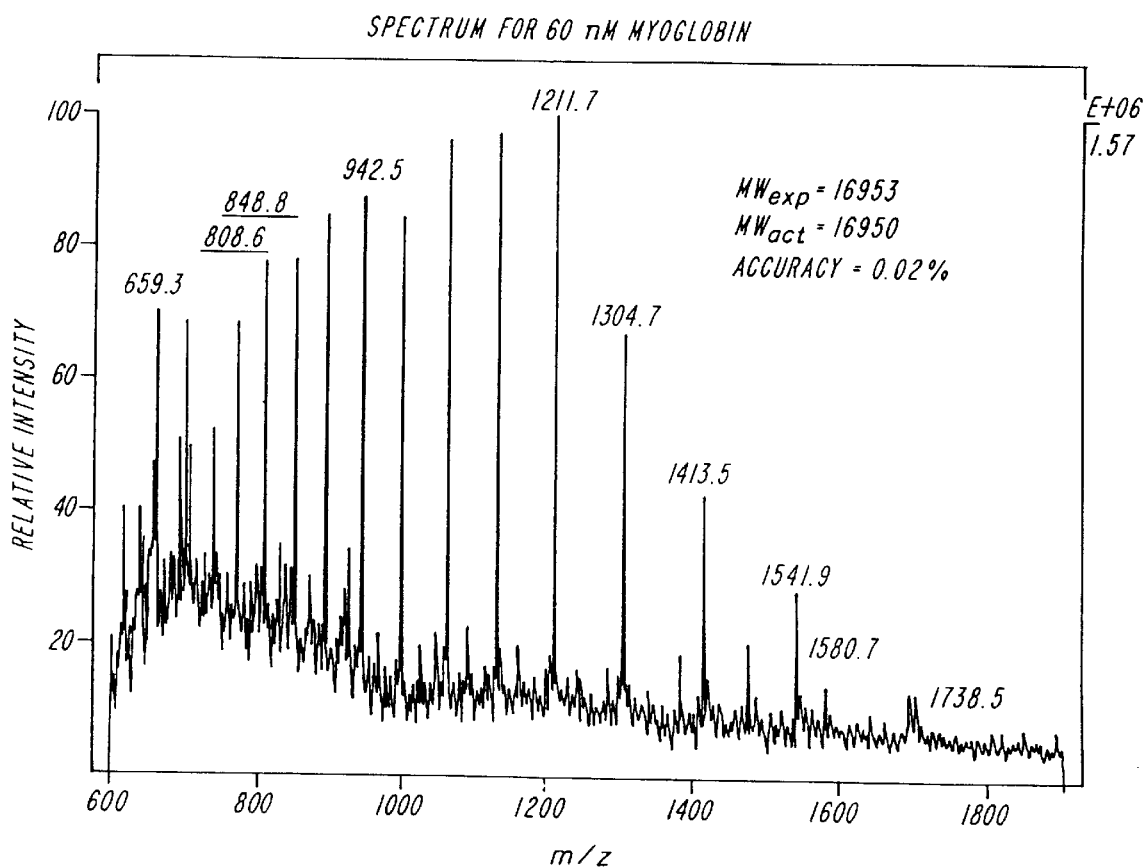
FIG. 9 shows an electrospray mass spectrum from ESI/MS detection of 0.001 mg/ml myoglobin in methanol/water/acetic acid (75/25/0.1)

FIG. 9 shows an electrospray mass spectrum of myoglobin obtained by spraying a 0.001 mg/ml myoglobin solution at 200 nl/min in methanol/water/acetic (75/25/0.1) directly from the exit port of the microdevice to the sampling orifice of the mass spectrometer. The signal to noise ratio in this example is better than 10:1, indicating that the limit of detection is better than $10^{-8}$M. The electrospray voltage was 4.4 kV.

EXAMPLE IV

Electrospray of a mixture of samples

Figure 10:
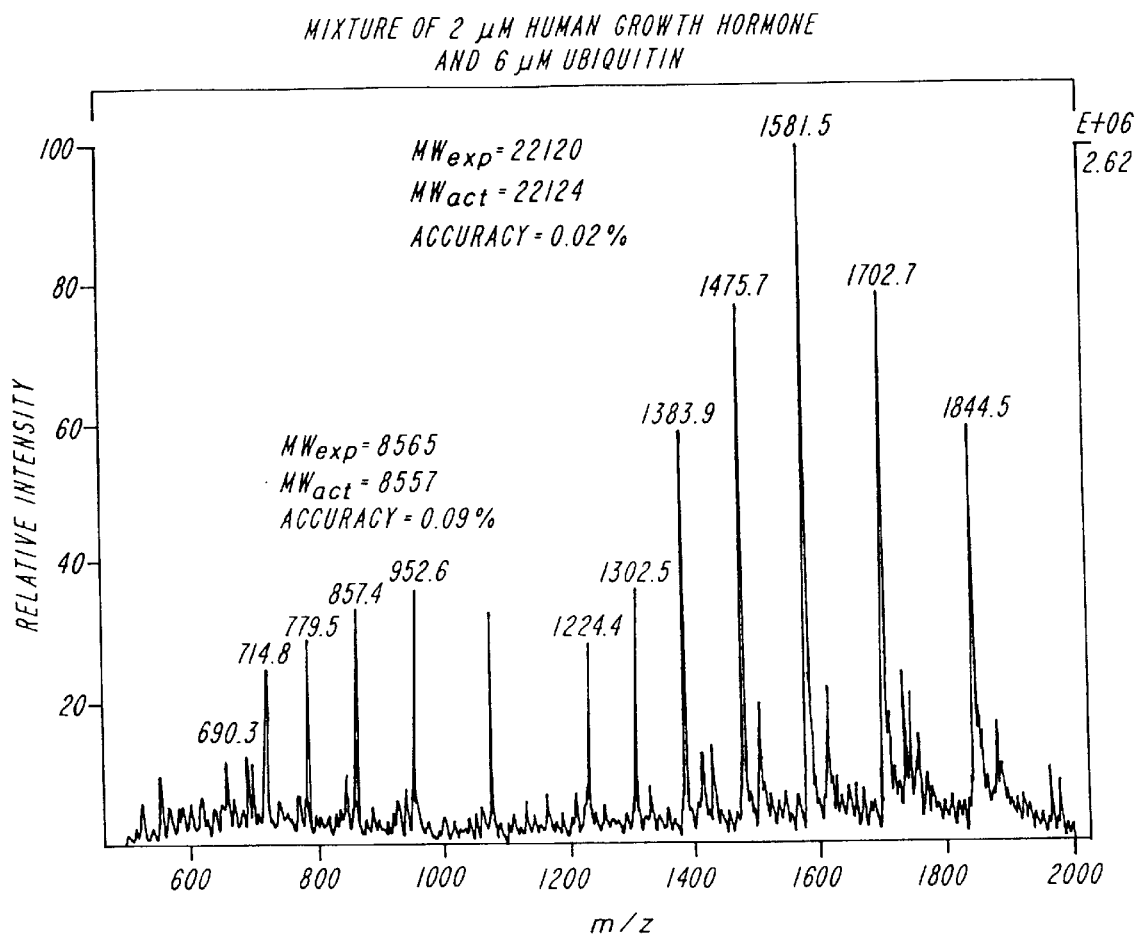
FIG. 10 shows an electrospray mass spectrum of a mixture of 0.05 mg/ml of human growth hormone and 0.05 mg/ml of ubiquitin, in methanol/water/acetic acid (75/25/0.1), infused from the microscale device of FIG. 1a, in a study of the detection limit using the device.

FIG. 10 shows a mass spectrum of a mixture of 0.05 mg/ml of human growth hormone and 0.05 mg/ml of ubiquitin in methanol/water/acetic acid (75/25/0.1) sprayed from micromachined chip channels of width 60 $\mu$m and depth 25 $\mu$m at a flow rate of 200 nl/min. The electrospray voltage (4.3 kV) was applied from the injection side of the chip. Two separate envelopes of multiply charged ions corresponding to individual sample components are visible in the spectrum. Exact molecular weight calculation of each sample component is possible from these data, and the experimentally determined MW values were the same as in Example II, when each sample was analyzed from a separate channel. This experiment illustrates that a complex mixture can be analyzed with only partial or even no separation of the sample components within the microdevice. The mass spectrometer serves as the separation tool. In separate experiments, MS/MS operation can be used to deduce the structure of individual ions.

EXAMPLE V

Analysis of a sample in aqueous solution

FIG. 11a shows an electrospray mass spectrum from infusing 0.05 mg/ml human growth hormone from aqueous solution, with methanol/water/acetic acid (75/25/0.1) in the syringe for applying pressure, and FIG. 11b shows an electrospray mass spectrum from infusing 0.05 mg/ml human growth hormone directly from a solution of methanol/water/acetic acid (75/25/0.1). This example shows that direct off-chip (off-microdevice) electrospraying of an aqueous sample without any prior addition of an organic solvent provides a high quality spectrum (FIG. 11a), comparable to the one obtained with a methanol supplemented sample (FIG. 11b), and that the same experimentally determined molecular weight value of 22,120 is obtained whether the sample is in an entirely aqueous or a methanol supplemented environment. In current practice with standard electrospray interfaces, samples are typically supplemented with organic additives; however, for biological samples which do not tolerate organic additives, direct spraying of an aqueous solution is the best approach to performing the analysis.

EXAMPLE VI

On-chip digestion of peptides and proteins

Figure 12A:
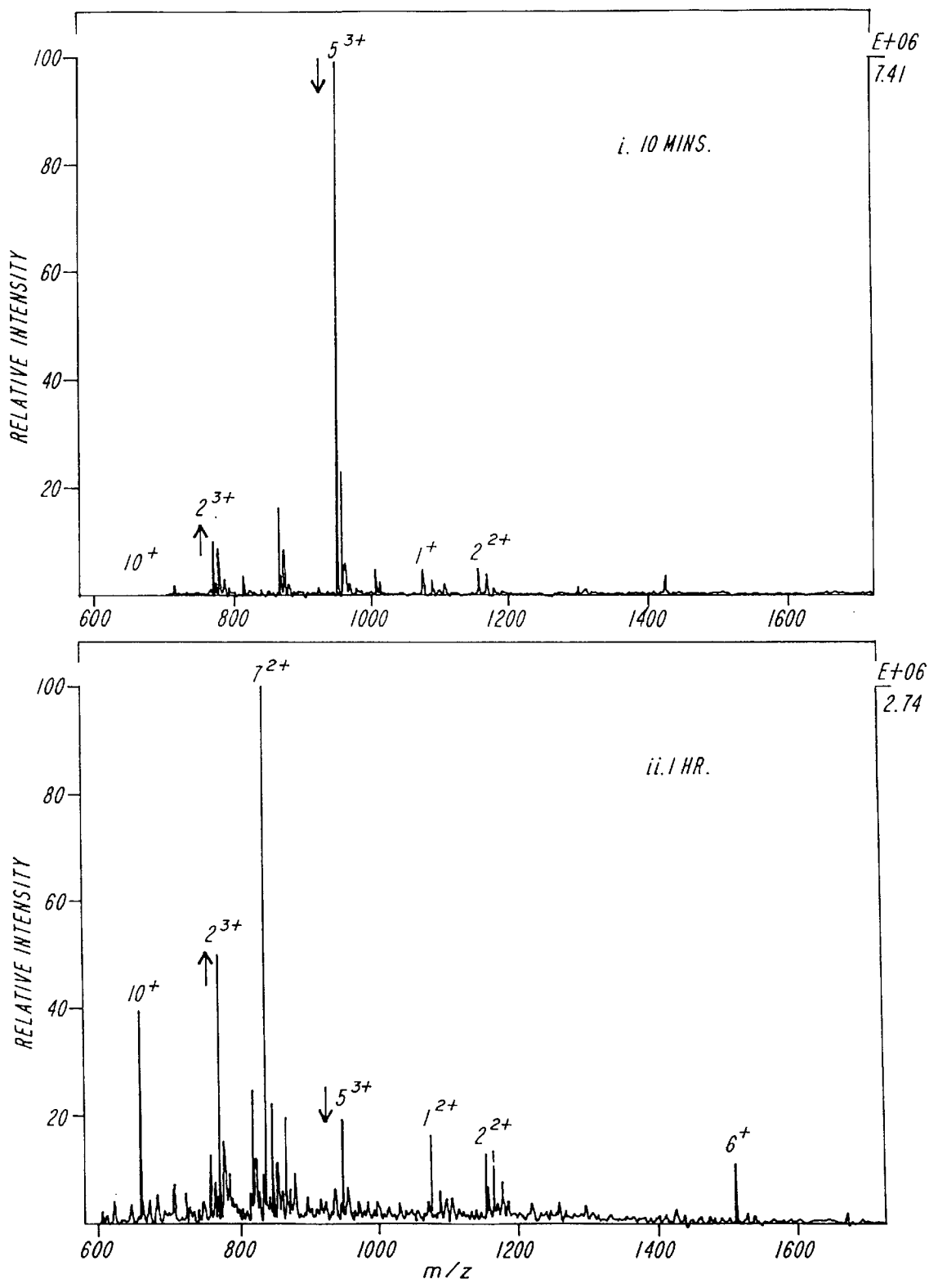
FIG. 12a, parts i and ii, show electrospray mass spectra of on-chip tryptic digest of melittin, at 30 $\mu$M in 20 mM Tris pH 8.2, melittin/trypsin ratio=300/1 (w/w), for two different time periods.

Referring to FIG. 12a, on-chip digestion of melittin was conducted in 20 mM Tris buffer of pH 8.2, melittin/trypsin ratio=300/1 (w/w). The concentration of melittin was 40 μM. Electrospray mass spectrum (i) is of a 10 min digestion, and spectrum (ii) is for a 1 hr digestion. The same sample fragments were detected, but at different levels, after the two digestion time periods. For example, peak no. 5, representing a molecular ion, is reduced after the longer digestion time period whereas peak no. 2, representing a product ion of the digestion, increases over time.

Figure 12B:
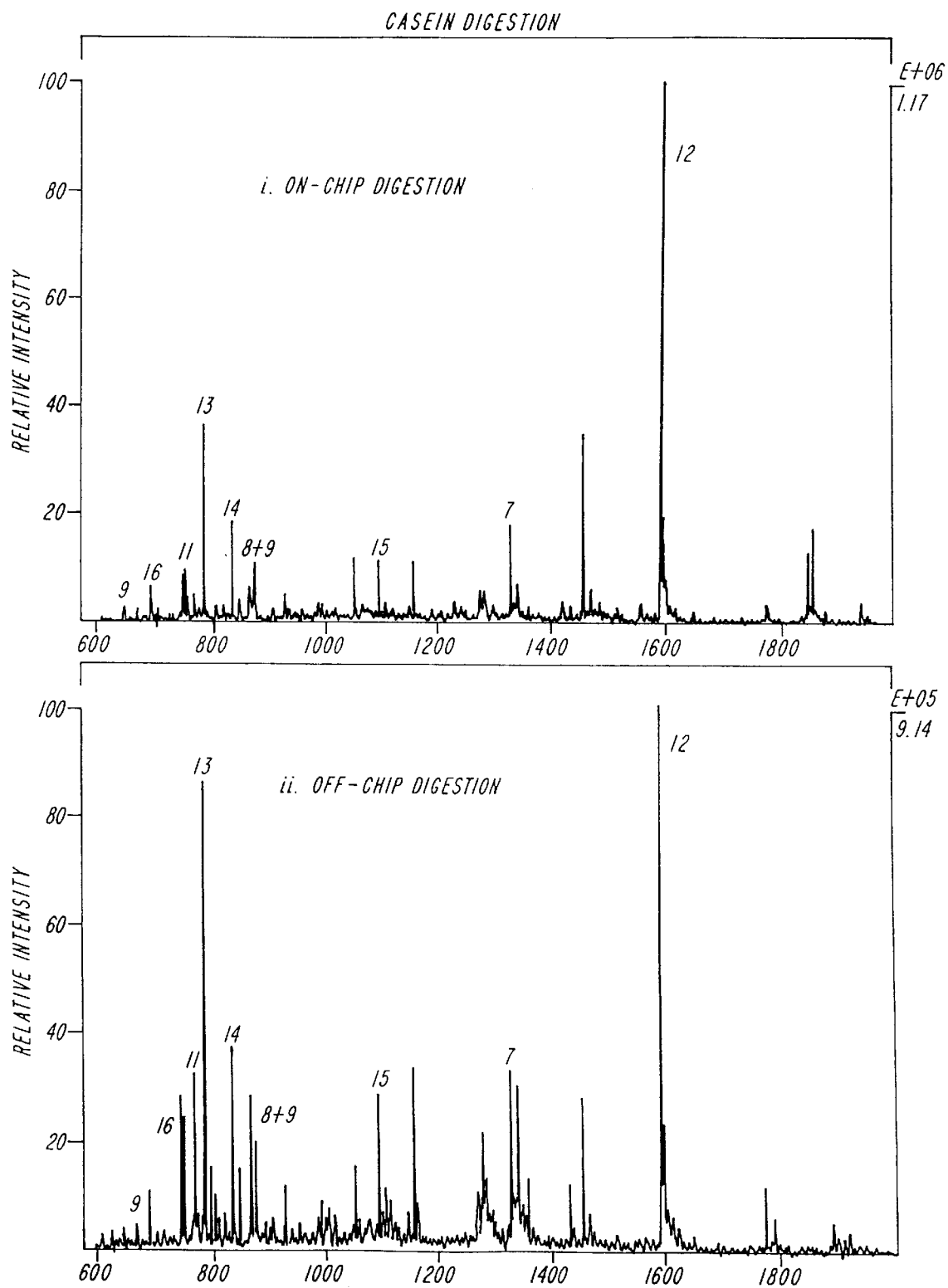
FIG. 12b, parts i and ii, show electrospray mass spectra of both on-chip and off-chip tryptic digests of casein, at 2 $\mu$M in 20 mM Tris pH 8.2, casein/trypsin ratio=60/1 (w/w)

FIG. 12b presents a comparison of on- and off-chip digestion of 2 μM casein. The reaction conditions were similar to those used in the experiment of FIG. 12a, except that the ratio of casein/trypsin was 60. The two spectra show substantially identical patterns. These results demonstrate that the microscale fluid handling system of the invention can be used to study the digestion kinetics of peptides and proteins and also show that on- and off-chip digestion generate very similar fragments. The success of on-chip digestion also indicates that incorporating sample preparation for electrospray mass spectrometry onto a chip is practical and will simplify the sample handling process and increase analysis throughput.

EXAMPLE VII

Analysis of a model DNA sample

Figure 13:
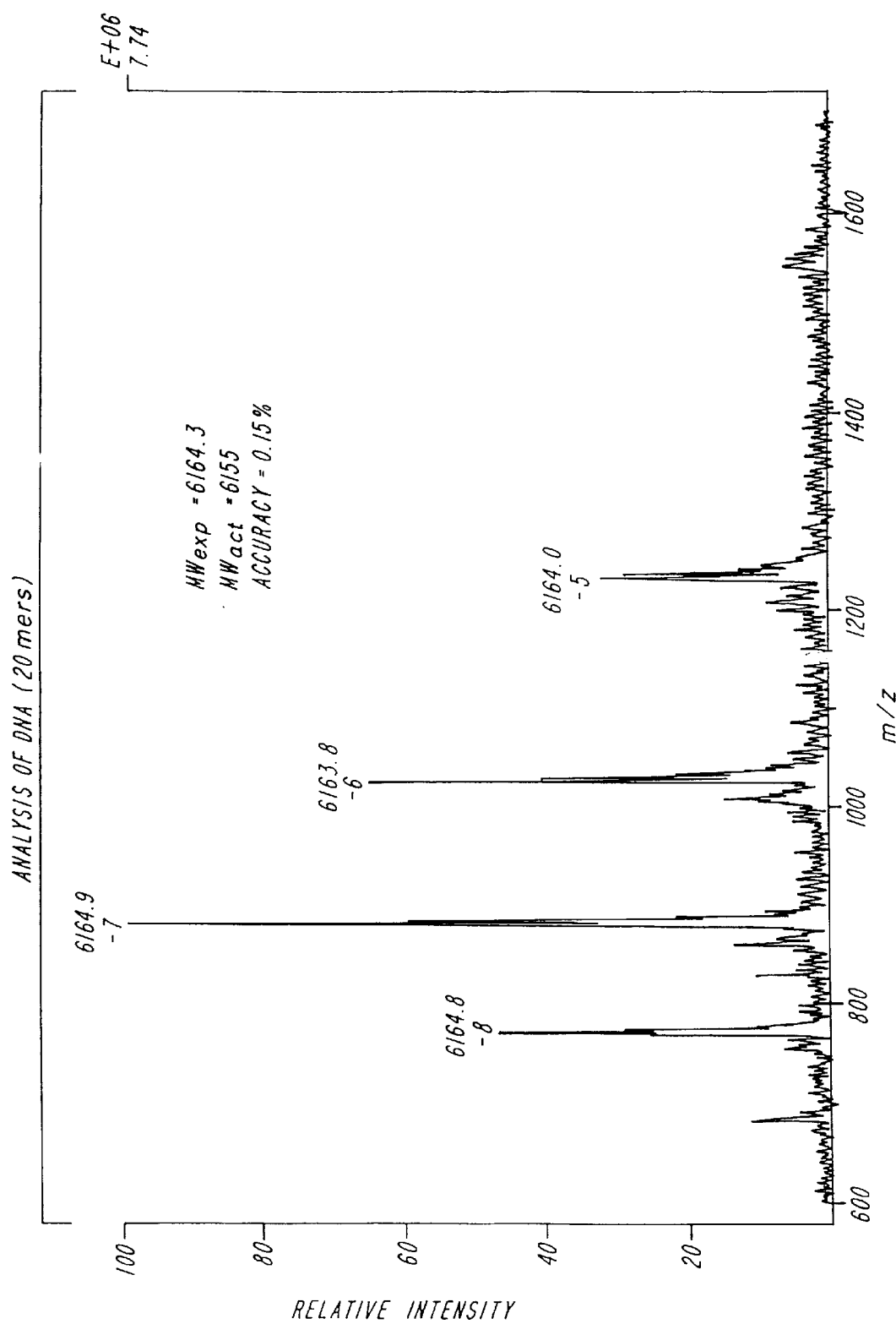
FIG. 13 shows an electrospray mass spectrum of a short DNA fragment (20 mer) in 60% acetonitrile, 40% $H_2O$.

To exploit the potential of the invention in analyzing varieties of samples, a short DNA fragment (20 mer) was analyzed by electrospray mass spectroscopy without any prior treatment, and the resulting spectrum is presented in FIG. 13. Compared to the calculated molecular weight of 6155, the experimentally measured molecular weight of the sample is 6164.3, an accuracy of within 0.015%. The DNA sample was sprayed from 60% acetonitrile, 40% $H_2O$ solution to facilitate the percentage of sample vaporization. With such a high accuracy in determining DNA molecular weight, it is contemplated that the invention can be analyzed to screen DNA mutations.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the appended claims and equivalents thereof.

What is claimed is:

1. A liquid handling system, comprising a microscale liquid handling substrate having one or more channels integrally formed therein, for conducting a liquid sample in said substrate, said one or more channels terminating in one or more exit ports in an outer surface of said substrate for transfer of a microscale quantity of a liquid sample off said substrate by droplet, spray or stream; and an external analytical and/or collection system, said system having an inlet that is proximate to but separate from said one or more exit ports of said microscale liquid handling substrate for receiving said microscale quantity of a liquid sample.

2. The system of claim 1 further comprising means for sample introduction into said one or more channels.

3. The system of claim 1 wherein said one or more exit ports in said outer surface of said substrate is recessed in said surface.

4. The system of claim 1 wherein said one or more exit ports in said outer surface of said substrate projects from said surface.

5. The system of claim 1 wherein said microscale liquid handling substrate is an optical grade material.

6. The system of claim 1 wherein said microscale liquid handling substrate is a non-conducting material.

7. The system of claim 1 wherein said microscale liquid handling substrate is a conducting material.

8. The system of claim 1 wherein a portion of a surface of said microscale liquid handling substrate between two of said exit ports is recessed.

9. The system of claim 1 wherein two or more of said channels in said microscale liquid handling substrate end in one of said one or more exit ports.

10. The system of claim 1 wherein a region of said microscale liquid handling substrate adjacent to said one or more channels is adapted for conducting sample chemistries or micropreparative or analytical operations on a microscale quantity of a fluid sample and for transferring a fluid sample from said region into said one or more channels.

11. The system of claim 1 wherein said microscale liquid handling substrate further comprises a reservoir or inlet port attached to said substrate and adapted for transferring a fluid into said one or more channels.

12. The system of claim 1 wherein said microscale liquid handling substrate has one or more first channels integrally formed therein for conducting a liquid sample and one or more second channels for conducting an additional fluid.

13. The system of claim 12 wherein said one or more second channels converge with one or more of said first channels at a common exit port.

14. The system of claim 1 wherein, in said microscale liquid handling substrate, said one or more exit ports are fabricated integrally with said substrate.

15. The system of claim 1 wherein, in said microscale liquid handling substrate, said one or more exit ports are fabricated separately from said substrate and attached to said termini of said channels.

16. The system of claim 1 wherein said external analytical and/or collection system is an external mass spectrometric analytical system.

17. The system of claim 1 wherein said external analytical and/or collection system is one or more collection systems.

18. A system for analyzing liquids, comprising a microscale liquid handling substrate having one or more channels integrally formed therein for conducting a liquid sample in said substrate, said one or more channels terminating in one or more exit ports in an outer surface of said substrate for transfer of a microscale quantity of a liquid sample off said substrate by electrospray ionization; and an external mass spectrometric analytical system, said system having an inlet that is proximate to but separate from said one or more exit ports of said microscale liquid handling substrate for receiving said microscale quantity of a liquid sample.

19. A liquid handling system, comprising a microscale liquid handling substrate having one or more channels integrally formed therein, for conducting a liquid sample in said substrate, said one or more channels terminating in one or more exit ports in an outer surface of said substrate for transfer of a microscale quantity of a liquid sample off said substrate by droplet, spray or stream; and an external collection system proximate to but separate from said one or more exit ports of said microscale liquid handling substrate for receiving said microscale quantity of a liquid sample.

20. A method for analyzing a liquid comprising the steps of:

providing a microscale liquid handling system comprising a substrate having one or more channels integrated in said substrate, said one or more channels terminating in one or more exit ports in an outer surface of said substrate;

loading a liquid sample into one of said one or more channels;

causing said liquid sample to travel in said channel in the direction of said exit port; and causing said liquid sample to exit said substrate through said exit port of said channel and transfer off said substrate by electrospray ionization to an inlet of a mass spectrometer, said inlet of said mass spectrometer being proximate to but separate from said exit port of said channel.

21. A method for processing microscale quantities of a liquid comprising the steps of:

providing a microscale liquid handling system comprising a substrate having one or more channels integrated in said substrate, said one or more channels terminating in one or more exit ports in an outer surface of said substrate;

loading a liquid sample into one of said one or more channels;

causing said liquid sample to travel in said channel in the direction of said exit port; and causing said liquid sample to exit said substrate through said exit port of said channel and transfer off said substrate by droplet, spray or stream to an external analytical and/or collection system, said system having an inlet that is proximate to but separate from said exit port.

22. The method of claim 21 wherein a portion of said surface adjacent to said exit port is coated with a material to prevent surface wetting by said liquid sample exiting said exit port.

23. The method of claim 21 wherein, in said step of causing said liquid sample to exit said substrate, said microscale liquid handling system is stationary in relation to said external analytical and/or collection system.

24. The method of claim 21 wherein, in said step of causing said liquid sample to exit said substrate, said microscale liquid handling system moves in relation to said external analytical and/or collection system.

25. The method of claim 21 wherein, prior to said step of causing said liquid sample to exit said substrate, said liquid sample or a component of said liquid sample is detected in said channel.

26. The method of claim 21 wherein said substrate further comprises a device for separating a liquid sample into components of said sample and said method further comprises the step of separating said sample into components of said sample.

27. The method of claim 26 wherein said device for separating a liquid sample into components of said sample is integrated in said substrate.

28. The method of claim 26 wherein said device for separating a liquid sample into components of said sample is detachably connected to said substrate.

29. The method of claim 26 wherein said one of said one or more channels comprises said device for separating a liquid sample into components of said sample.

30. The method of claim 21 wherein said substrate further comprises a device for causing digestion of a sample and said method further comprises the step of digesting said sample.

31. The method of claim 21 wherein said substrate further comprises a device for desalting a sample and said method further comprises the step of desalting said sample.

32. The method of claim 21 wherein said substrate further comprises a device for preconcentrating a sample and said method further comprises the step of preconcentrating said sample.

33. The method of claim 21 wherein said substrate further comprises a device for carrying out affinity binding on a sample and said method further comprises the step of carrying out affinity binding on said sample.

34. The method of claim 21 wherein said substrate further comprises a device for size exclusion chromatography and said method further comprises the step of carrying out size exclusion chromatography on said sample.

35. The method of claim 21 wherein said substrate has one or more first channels integrally formed therein for conducting a liquid sample and one or more second channels for conducting an additional fluid.

36. The method of claim 35 wherein, in said substrate, said one or more second channels converge with one or more of said first channels at a common exit port.

37. The method of claim 35 wherein said one or more second channels in said substrate conducts an additional fluid which is added to said microscale quantity of a liquid sample so that said additional fluid functions as a fluid sheath.

* * * * *